United States Patent
Hagelstrom

(10) Patent No.: US 11,079,378 B2
(45) Date of Patent: Aug. 3, 2021

(54) DETECTION OF ANALYTES IN BODILY FLUID TO DETERMINE THE INITIATION OF PARTURITION

(71) Applicant: Xpecting Diagnostics, Inc., San Diego, CA (US)

(72) Inventor: R. Tanner Hagelstrom, San Diego, CA (US)

(73) Assignee: Xpecting Diagnostics, Inc., San Diego, CA (US)

( * ) Notice: Subject to any disclaimer, the term of this patent is extended or adjusted under 35 U.S.C. 154(b) by 863 days.

(21) Appl. No.: 15/534,287

(22) PCT Filed: Dec. 10, 2015

(86) PCT No.: PCT/US2015/065099
§ 371 (c)(1),
(2) Date: Jun. 8, 2017

(87) PCT Pub. No.: WO2016/094722
PCT Pub. Date: Jun. 16, 2016

(65) Prior Publication Data
US 2017/0363621 A1    Dec. 21, 2017

Related U.S. Application Data

(60) Provisional application No. 62/090,080, filed on Dec. 10, 2014.

(51) Int. Cl.
*G01N 33/558*    (2006.01)
*C12Q 1/00*    (2006.01)
*G01N 33/68*    (2006.01)

(52) U.S. Cl.
CPC .............. *G01N 33/558* (2013.01); *C12Q 1/00* (2013.01); *G01N 33/689* (2013.01);
(Continued)

(58) Field of Classification Search
CPC ...... G01N 33/558; G01N 33/689; C12Q 1/00; C12Q 2537/125; C12Q 2525/205; C12Q 2525/207
See application file for complete search history.

(56) References Cited

U.S. PATENT DOCUMENTS 5,252,496 A * 10/1993 Kang ............... G01N 33/54366
436/529
5,773,234 A * 6/1998 Pronovost ............ G01N 33/558
435/7.2
(Continued)

FOREIGN PATENT DOCUMENTS

WO    2010/017201 A1    2/2010
WO    2012/129650 A1    10/2012

OTHER PUBLICATIONS

Abe et al., Aptamer sensors combined with enzymes for highly sensitive detection, Biosensors-Emerging Materials and Applications. InTech, 2011, pp. 227-242.
(Continued)

*Primary Examiner* — Christopher L Chin
(74) *Attorney, Agent, or Firm* — Dorsey & Whitney LLP

(57) ABSTRACT

Devices and kits for detecting molecular targets involved in the onset of parturition are presented, as are methods of using the same. The devices and kits include one or more associators specific for molecular targets, such as microRNAs and proteins and peptide fragments thereof. The associators, such as aptamers or antibodies, bind their targets, when such targets are present in a fluid sample from a pregnant woman, to produce a detectable signal. The signal may be produced in a lateral flow device.

16 Claims, 16 Drawing Sheets

(52) U.S. Cl.
CPC . *C12Q 2525/205* (2013.01); *C12Q 2525/207* (2013.01); *C12Q 2537/125* (2013.01)

(56) References Cited

U.S. PATENT DOCUMENTS

| | | | |
|---|---|---|---|
| 6,485,982 | B1 | 11/2002 | Charlton et al. |
| 7,709,272 | B2 * | 5/2010 | Fuks .................... G01N 33/558 |
| | | | 436/514 |
| 8,216,784 | B2 | 7/2012 | Taylor et al. |
| 8,637,254 | B2 | 1/2014 | Taylor et al. |
| 2014/0011193 | A1 | 1/2014 | Heemstra |
| 2014/0186332 | A1 | 7/2014 | Ezrin et al. |
| 2014/0315195 | A1 | 10/2014 | Wong et al. |

OTHER PUBLICATIONS

Condon et al., Surfactant protein secreted by the maturing mouse fetal lung acts as a hormone that signals the initiation of parturition, Proceedings of the National Academy of Sciences of the United States of America, 101, 2004, pp. 4978-4983.

Lutz et al., Dissolvable Fluidic Time Delays For Automated Paper Diagnostics, 16th International Conference on Miniaturized Systems for Chemistry and Life Sciences, Oct. 28-Nov. I, 2012, Okinawa, Japan, pp. 788-790.

Mendelson, Minireview: Fetal-Maternal Hormonal Signaling in Pregnancy and Labor, Molecular Endocrinology, vol. 23, 2009, pp. 947-954.

Renthal et al., miR-200 family and targets, ZEB1 and ZEB2, modulate uterine quiescence and contractility during pregnancy and labor, Proceedings of the National Academy of Sciences, vol. 107, No. 48, 2010, pp. 20828-20833.

Shynlova et al., Integration of endocrine and mechanical signals in the regulation of myometrial functions during pregnancy and labor, European Journal of Obstetrics & Gynecology and Reproductive Biology, 144, 2009, pp. S2-S10.

Zen et al., Circulating microRNAs: a novel class of biomarkers to diagnose and monitor human cancers. Medicinal research reviews, 32, 2012, pp. 326-348.

Zhao et al., Circulating MicroRNA miR-323-3p as a Biomarker of Ectopic Pregnancy, Clinical Chemistry, vol. 58, No. 5, 2012, pp. 1-16.

International Search Report dated Feb. 23, 2016, in PCT Application No. PCT/US2015/065099, 3 pages.

Written Opinion dated Feb. 23, 2016, in PCT Application No. PCT/US2015/065099, 6 pages.

* cited by examiner

DETECTION OF ANALYTES IN BODILY FLUID TO DETERMINE THE INITIATION OF PARTURITION

CROSS-REFERENCE TO RELATED APPLICATIONS

This application is a national stage application under 35 U.S.C. § 371 of International Application No. PCT/US2015/065099, filed Dec. 10, 2015, entitled "Detection of Analytes in Bodily Fluid to Determine the Initiation of Parturition," which claims the benefit of U.S. Provisional Application No. 62/090,080, filed Dec. 10, 2014, each of which is incorporated herein by reference in its entirety.

TECHNICAL FIELD

The technology described herein relates to devices and kits for predicting the initiation of parturition and methods of using the same.

BACKGROUND

The average gestation period of a healthy human pregnancy in a nulliparous mother giving birth spontaneously is 41 weeks and 3 days, while it is 41 weeks and 1 day for multiparous mothers. The time range for normal gestation is considered to be 38 to 42 weeks. At 37 weeks pregnancy is considered near-term, while anything before 37 weeks is considered pre-term. Thus, there are 4 weeks or 28 days of uncertainty with respect to the onset of labor within what is considered the normal gestational period, and up to 5 weeks or 35 days of uncertainty from the time pregnancy enters near-term status.

Common early warning signs that may precede the onset of labor include release of mucus plugging the cervix, vaginal bleeding, poorly coordinated contractions, back pain, and loose stools. These symptoms may precede the onset of labor in a highly variable time frame ranging from weeks to hours. Some of the warning signs may arise for reasons other than the onset of labor and can be mistakenly interpreted. No symptoms are experienced universally or interpreted universally. No accurate predictor of or test for the onset of labor currently exists.

The information included in this Background section of the specification, including any references cited herein and any description or discussion thereof, is included for technical reference purposes only and is not to be regarded as subject matter by which the scope of the present disclosure as defined in the claims is to be bound.

SUMMARY

The technology disclosed herein relates to devices and kits for predicting the initiation of parturition, and methods of using the same. The devices, kits, and methods enable a pregnant woman to determine if she will go into labor within a given time period.

The devices may be lateral flow devices that detect molecular targets involved in the onset of parturition. The lateral flow devices comprise a backing, membrane, sample pad, conjugate pad, capture pad, and absorbent pad. A sample of bodily fluid, such as urine or blood, from a pregnant woman applied to the sample pad flows by capillary action through the conjugate pad and capture pad to the absorbent pad. Associators, which may be aptamers or antibodies or both, immobilized in the device bind to their target molecules as the sample flows through the device. The accumulation of associators and their targets in the capture pad produces detectable signals that may indicate if the initiation of parturition is near.

In some embodiments, first associators, which may be aptamers or antibodies or both, are releasably bound to the conjugate pad. The first associators may be conjugated to reporter molecules, such as gold nanoparticles or latex, to enable the detection of associators. In some embodiments, the first associators are specific for molecules involved in the initiation of parturition. In some embodiments, the molecules are microRNAs or proteins, or peptide fragments thereof, the expression levels of which are increased or decreased near the initiation of parturition. In some embodiments, the up-regulated microRNAs include miR-429, miR-200a, and miR-200b, and in some embodiments, the down-regulated microRNAs include miR-199a-3p and miR-214. In some embodiments, the first associators are specific for control microRNAs or proteins, or peptide fragments thereof. In some embodiments, the first associators form complexes with their target molecules.

In some embodiments, second associators, which may be aptamers or antibodies or both, are immobilized on the capture pad. In some embodiments, each second associator is specific for a complex of a first associator and the molecule to which the first associator is bound.

In some embodiments, the sample comprises exosomes comprising microRNA target molecules. In some embodiments, the exosomes are lysed, such as by a detergent, in a delay zone in the sample pad. In other embodiments, a vessel and detergent solution are provided with the lateral flow device. The sample is added to the vessel and the detergent solution lyses the exosomes to release the microRNAs before the sample is applied to the lateral flow device. In some embodiments, a kit is provided comprising a lateral flow device, a vessel, and detergent solution.

In some embodiments, a lateral flow device for predicting the initiation of parturition comprises a plurality of first associators capable of binding a molecule involved in the initiation of parturition and a plurality of second associators; more than one type of first associator may be present within the first plurality (for example, two distinct types of first associators, three types of associators, etc.) such that more than one type of molecule involved in the onset of parturition is able to be bound; in the same manner, more than one type of second associator may also be present within the second plurality; the first and second associators are independently selected from aptamers and antibodies and when more than one type of associator is present within a plurality, each type is independently selected from an aptamer and an antibody (for example, three distinct types of first associator may be present, the first being a first antibody, the second being a first aptamer, and the third being a second antibody); the molecule involved in the initiation of parturition may be a microRNA, a protein, or a peptide fragment of the protein; it is possible that more than one type of molecule may be present in a sample, in which case they may be any combination of microRNAs, proteins, and peptide fragments of the proteins; the expression level of at least one type of molecule may be increased in the initiation of parturition, and the molecule may be a microRNA selected from miR-429, miR-200a, and miR-200b; at least one type of molecule may be decreased in the initiation of parturition, and the molecule may be a microRNA selected from miR-199a-3p and miR-214; each associator in the plurality of first associators may be conjugated to a reporter molecule, and the reporter molecule may be selected from a gold nanoparticle and latex; each associator in the plurality of second associators may be capable of binding a complex of the first associator bound to the molecule; the device may comprise a conjugate pad to which the plurality of first associators are releasably bound; the device may comprise a capture pad to which the the plurality of second associators are fixedly bound; the device may comprise a sample pad configured to receive a fluid sample, which may be selected from urine, blood, saliva, plasma, amniotic fluid, and peritoneal fluid; the sample may comprise exosomes, and the device may comprise a delay zone comprising an exosome-lysing detergent.

In some embodiments, a method of using a lateral flow device, such as to predict the initiation of parturition, is provided. A user applies a sample to the device, after which the user may not need to provide further input and may await results. During the processing period, first associators bind to target molecules within the sample to form first complexes. The first associators may be conjugated to reporter molecules. Second associators bind the first complexes to form second complexes. The accumulation of second complexes produces a detectable signal, which may be a visually detectable signal. The signal indicates if the initiation of parturition is or is not near.

In some embodiments, a method of predicting the initiation of parturition comprises contacting molecules in a sample with a plurality of first associators to form first complexes, and contacting the first complexes with a plurality of second associators to form second complexes, and the production of second complexes produces a signal; the accumulation of second complexes may produce a detectable signal, such as a visibly detectable signal; more than one type of first associator may be present within the first plurality as described above; similarly, more than one type of second associator may be present within the second plurality as described above; the first associators may be conjugated to reporter molecules; the method may also comprise incubating the sample in an exosome-lysing detergent prior to contacting with the plurality of first associators.

In some embodiments, a kit for predicting the initiation of parturition comprises a lateral flow device, a vessel configured to receive a fluid sample, a detergent solution, and instructions for using the device; the lateral flow device may comprise a backing affixed to each of a sample pad, a conjugate pad, a capture pad, and a wick, and may be a device for predicting the initiation of parturition disclosed herein.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present disclosure as defined in the claims is provided in the following written description of various embodiments of the present disclosure and illustrated in the accompanying drawings.

DETAILED DESCRIPTION

Figure 1:
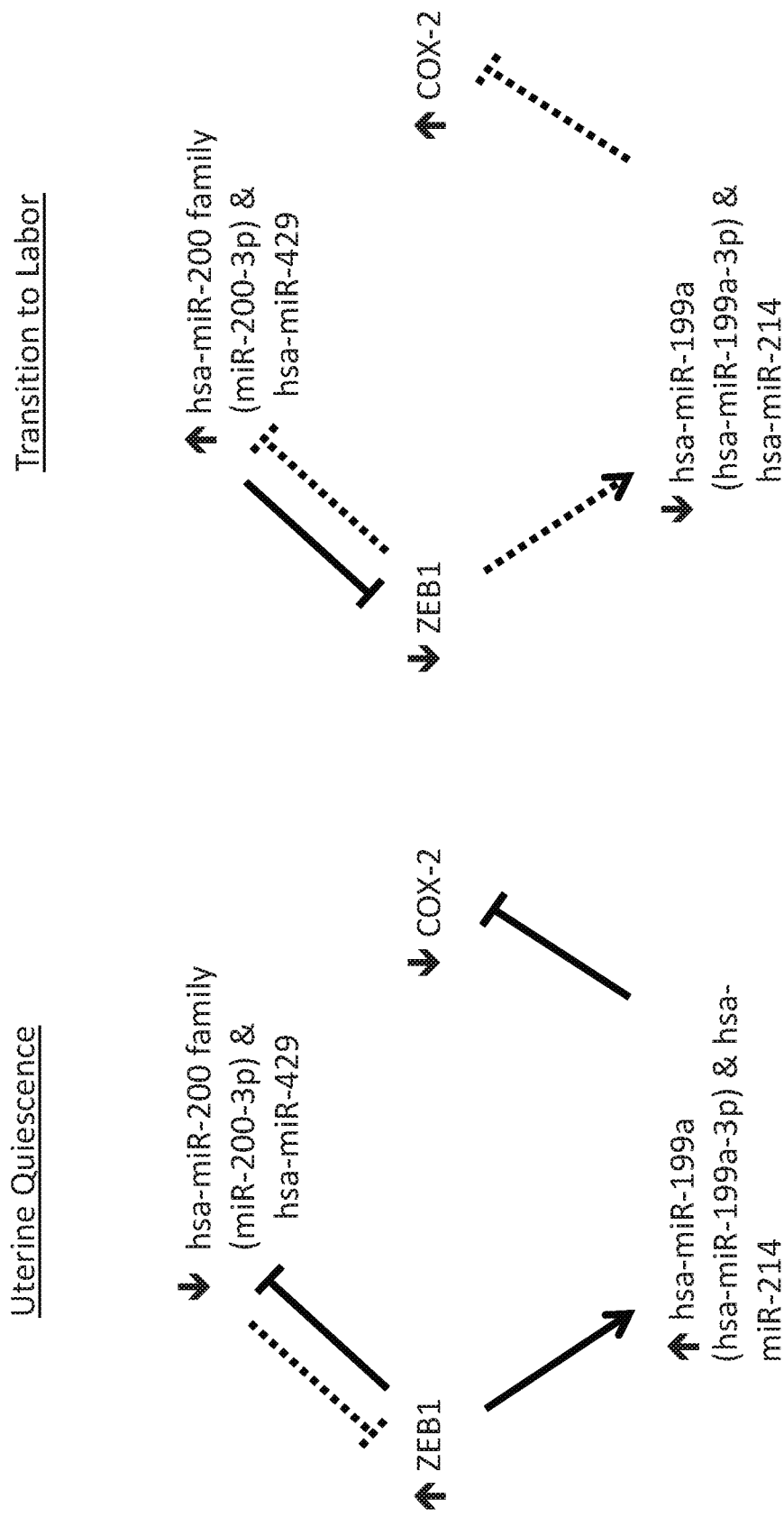
FIG. 1 is a schematic diagram of microRNA control of myometrium contraction.

Devices and kits for, and methods of, detecting molecular targets involved in the onset of parturition are disclosed herein. The devices may be generally understood as having a first associator specific for a first target and a second associator specific for a second target. The presence of a parturition-associated molecular target in a sample of bodily fluid applied to the devices yields a detectable signal. In some implementations, the signal may indicate that parturition will or will not commence within a certain time period.

In some embodiments, the associators are either aptamers or antibodies or both. A first associator may be specific for a first target, and a second associator may be specific for a complex of a first associator and a first target. In some implementations, the first associators and the second associators are permanently or releasably bound to a lateral flow device.

The first targets may be microRNAs or proteins or peptide fragments thereof. The microRNAs may occur naturally in exosomes of bodily fluids, such as urine or blood, of near-term pregnant women.

In some embodiments, a sample of bodily fluid comprising microRNA-containing exosomes is applied to a lateral flow device described herein. The sample may be applied to a sample pad, which may comprise a matrix that delays fluid flow and may also comprise detergents capable of lysing exosomes. While the sample is delayed, detergents may lyse the exosomes to release the microRNAs, which may be microRNAs up- or down-regulated near the onset labor, control (housekeeping) microRNAs, or a combination thereof. In some embodiments, exosomes from a sample of bodily fluid are lysed in a vessel comprising detergents prior to being applied to a sample pad of a lateral flow device.

The microRNAs may then migrate via capillary action to a conjugate pad. The conjugate pad may include releasably immobilized first associators, which may be aptamers or antibodies, specific to some of the microRNAs. The aptamers or antibodies may be bound to reporter molecules, such as gold nanoparticles or latex. As the fluid sample migrates to and through the conjugate pad, aptamers or antibodies may bind their target microRNAs to form aptamer:microRNA or antibody:microRNA complexes, respectively.

The aptamer:microRNA or antibody:microRNA complexes may then flow by capillary action to a capture pad, which may include a test zone and a control zone. Each of the test zone and control zone may include immobilized second associators, which may be aptamers or antibodies, specific to the complexes.

The immobilized second aptamers or antibodies bind their target complexes, which may result in the accumulation of complexes within the test zone or control zone or both. Concomitant accumulation of reporter molecules conjugated to the first aptamers or antibodies in the complexes may produce a visually detectable signal, such as a colored line.

In some embodiments, control and labor-associated up-regulated microRNAs are targeted, and the absence of a line in the test zone but the presence of a line in the control zone indicates that threshold levels of up-regulated microRNAs were not present in the sample, and that the onset of labor is not near. In some embodiments, control and labor-associated up-regulated microRNAs are targeted, and a line in each of the test and control zones indicates threshold levels of up-regulated microRNAs were present in the sample, and the onset of labor is near.

In some embodiments, labor-associated up- and down-regulated microRNAs are targeted, and a line in the test zone but not in the control zone indicates one or more up-regulated microRNAs were present in the sample, and the onset of labor is near. In some embodiments, labor-associated up- and down-regulated microRNAs are targeted, and a line in the control zone but not in the test zone indicates the presence of one or more down-regulated microRNAs, and the onset of labor is not near. In some embodiments, labor-associated up- and down-regulated microRNAs are targeted, and a line in each of the test and control zones indicates the presence of both up- and down-regulated microRNAs, and that the onset of labor is near.

In some embodiments, the presence of absence of signals may indicate a specific timeframe for the onset of labor, such as that it will commence within 48 hours or will not commence within 24 hours.

As used herein, "microRNA" includes both the precursor forms and the mature (processed) forms from any mammalian species, including humans. The prefix "miR" is used herein to refer to both precursor and mature forms, although "mir" typically refers to the precursor form and "miR" typically refers to the mature form. The prefix "mir" is used herein to refer to precursor forms. The suffixes "-3p" and "-5p" are used herein to refer to mature microRNAs derived from the 3-prime arm and 5-prime arm, respectively, of a precursor microRNA. When no suffix is used, the microRNA includes either or both the -3p and -5p forms. When used, the prefix "hsa" refers specifically to human-derived sequences or molecules.

As used herein, the initiation (or onset or commencement) of parturition means the point during pregnancy at which, under normal circumstances, the process of childbirth becomes irreversible. The transition is governed by a molecular signaling cascade, and the presently disclosed devices, kits, and methods detect, directly or indirectly, the presence of one or more components of the cascade to predict the initiation of parturition or onset of labor.

Detection Targets

Detection targets are components of the molecular signaling cascade that can be used to predict the onset of parturition. Any molecule that is directly or indirectly involved in the onset of parturition may be a detection target. In one embodiment, the target is a microRNA, the expression of which is up- or down-regulated near the onset of parturition.

In another embodiment, the target is a protein, or peptide fragment thereof, that influences the up- or down-regulation of one or more microRNAs near the onset of parturition. In another embodiment, the target is a complex of an associator (described below) and another target (a first associator:first target complex, described below). In another embodiment, the target is a complex of an aptamer and another target (a first aptamer:first target complex described below). In another embodiment, the target is a complex of an antibody and another target (a first antibody:first target complex described below).

Without being limited to any mechanism or mode of action, the progesterone signaling pathway helps maintain uterine quiescence during most of human pregnancy through increased expression of both circulating progesterone ($P_4$) and progesterone receptor (PR). Transition to labor is associated with a pro-inflammatory cascade in response to mechanical and hormonal signals from both the mother and fetus that ultimately impair PR function. Specifically, increased levels of estradiol-17β ($E_2$) and enhanced activity of estrogen receptor (ER)-α oppose the anti-inflammatory activity of $P_4$/PR, at least in part because in humans there is no reduction of systemic $P_4$ near-term or during the onset of labor. Ultimately, pro-inflammatory cytokines, such as Tumor Necrosis Factor (TNF)-α, lead to increased expression of contraction-associated proteins (CAPS) when PR function is inactivated. One CAP, the cyclooxygenase (COX)-2 enzyme, helps effect the stimulation of an activated myometrium by catalyzing the production of pro-inflammatory, contraction-inducing stimulatory prostaglandins.

Zinc finger E-box binding homeobox (ZEB) 1 helps mediate the antagonistic effects of $P_4$ and $E_2$ on myometrial contractility during human pregnancy and labor. As shown in FIG. 1, ZEB1 functions at least in part by regulating several different microRNAs. Specifically, the levels of the miR-200 family and miR-429 increase in myometrial cells preceding stimulation of an activated myometrium while the levels of the miR-199 family and miR-214 (either miR-214-3p or miR-214-5p, or both) decrease. The miR-200 family may include, but is not limited to, miR-200, miR-200a, miR-200b, miR-200b-3p, and miR-200b-5p. The miR-199 family may include, but is not limited to, miR-199, miR-199a, miR-199a-3p, and miR-199a-5p.

Levels of the miR-200 family of microRNAs are low during uterine quiescence, but their expression increases in the myometrium near the onset of labor. ZEB1 blocks the expression of the miR-200 family of microRNAs. However, miR-200 microRNAs target ZEB1 in a positive-feedback loop. Thus, when the ratio of [$E_2$/ER:$P_4$/PR] shifts towards increasing $E_2$/ER, ZEB1 levels begin to decrease and this trend is enforced by increasing levels of miR-200 family microRNAs. Further, ZEB1 enforces expression of two microRNAs, miR-199a-3p and miR-214, which directly target and down-regulate COX-2. Thus, miR-199a-3p/miR-214 levels fall with ZEB1 levels, resulting in the induction of COX-2 expression.

The expression changes of microRNAs such as miR-200 miRNAs, miR-429, miR-199a, and miR-214 govern and precede the induction of uterine contraction. These microRNAs regulate contraction-associated gene expression in a sequence-specific manner by modulating the translation of and/or cellular levels of messenger RNAs (mRNAs), which results in changes in expression levels of the corresponding proteins.

Detection targets may be microRNAs that are up-regulated near the onset of parturition (hereinafter, "first targets-up"). First targets-up include, but are not limited to, miR-429 and the miR-200 family, such as miR-200a, miR-200b, and miR-200b-3p. MicroRNAs that are down-regulated near the onset of parturition (hereinafter, "first targets-down") may also be detection targets. First targets-down include, but are not limited to, miR-199a-3p and miR-214.

Further examples of detection targets are proteins, or peptide fragments thereof, that regulate microRNAs that are involved in the onset of parturition. These proteins include, but are not limited to, estrogen, COX-2, and ZEB1 and/or ZEB2.

Still further examples of detection targets are first associator:first target complexes (described in greater detail below). Complexes include, but are not limited to, aptamer:miR-429, aptamer:miR-200a, aptamer:miR-200b, aptamer:miR-199a-3p, aptamer:miR-214, aptamer:estrogen, aptamer:COX-2, aptamer:ZEB1, aptamer:ZEB2, antibody:miR-429, antibody:miR-200a, antibody:miR-200b, antibody:miR-199a-3p, antibody:miR-214, antibody:estrogen, antibody:COX-2, antibody:ZEB1, and antibody:ZEB2.

Analytes (microRNAs and proteins, or peptide fragments thereof, involved in the initiation of parturition) may be present and detectable in a bodily fluid. Bodily fluids may include urine, blood, saliva, plasma, amniotic fluid, and peritoneal fluid. MicroRNAs may be present in exosomes (also known as membrane fragments, membrane vesicles, and microvesicles) within a bodily fluid.

The time period during which detection targets are detectable in a bodily fluid may vary depending on the target and/or the fluid. In one embodiment, a first target-up is detectable during the 6 hours immediately prior to the onset of labor. In another embodiment, a first target-up is detectable during the 12 hours immediately prior to the onset of labor. A first target-up may also be detectable during the 24, 36, 48, 60, 72, 84, or 96 hours immediately prior to the onset of labor.

In another embodiment, a first target-down is detectable up until 96 hours before the onset of labor. In another embodiment, a first target-down is detectable up until 84 hours before the onset of labor. A first target-down may also be detectable up until 72, 60, 48, 36, 24, 12, or 6 hours before the onset of labor.

Associators

The presently disclosed devices, kits, and methods include at least one associator that associates with a detection target (described above). An associator may covalently or non-covalently bind or otherwise couple with a detection target.

In some embodiments, an associator is an aptamer. In some embodiments, an associator is an antibody. In each set of a first associator and related second associator, the two associators may be of the same type of different types. For example, in some embodiments a first associator and related second associator may both be aptamers. In other embodiments, a first associator and related second associator may both be antibodies. In some embodiments, the first associator may be an aptamer and the related second associator may be an antibody. In other embodiments, the first associator may be an antibody and the related second associator may be an aptamer.

A first associator may be specific for a first target and may associate with the first target to form a first associator:first target complex. For example, a first associator may be an aptamer that specifically binds to a first target-up, such as miR-429, to form an aptamer:miR-429 complex. A second associator may be specific for a complex of a first associator and a first target and may associate with the complex to form a second associator:(first associator:first target) complex. For example, a second associator may be an antibody that specifically binds to an aptamer:miR-429 complex to form an antibody:(aptamer:miR-429) complex.

In an assay for determining the onset of parturition, an associator may aid in direct or indirect detection of a first target. For example, a first associator may be conjugated to a reporter molecule (described below).

Development of Aptamers

In some embodiments, an associator is an aptamer. One or more aptamers may be developed against one or more detection targets. The presently disclosed aptamers may be single-stranded DNA and/or RNA nucleic acids. In one embodiment, an aptamer is 15-60 nucleotides in length. In another embodiment, an aptamer is 40-50 nucleotides in length. In another embodiment, an aptamer is approximately 45 nucleotides in length. Aptamers may be developed by any method known in the art, such as in vitro selection or systematic evolution of ligands by exponential enrichment (SELEX) or similar methods as described in Oliphant et al. (*Mol. Cell Biol.* 1989, 9:2944-2949), Tuerk & Gold (*Science* 1990, 249:505-510), Ellington & Szostak (*Nature* 1990, 346:818-822), and Lee et al. (*Mol. Ther.* 2013, 21:1004-1013). Aptamer development may include selection of oligonucleotides that bind specifically to a target (described below) from a large library of random nucleic acid sequences.

Nucleosides in aptamers may be naturally occurring or may be modified. Modified nucleosides may be present during the development stage, such as in the library of random nucleic acid sequences. Some or all of the nucleosides may be modified after identification of an aptamer that binds a target. Modifications may increase binding affinity, decrease target off-rate, and/or facilitate detection. For example, chemical modifications of aptamers may facilitate visualization in lateral flow devices.

The presently disclosed aptamers may be developed in a single-step or multi-step process. In a single step process, aptamers are developed against a target, such as a microRNA, protein, or peptide. The aptamer may bind the target as an aptamer:target complex. Multiple aptamers may be developed against the same or different regions of a single target. When the target is of large enough size, such as a protein or peptide, the target may be bound simultaneously by more than one molecule at more than one site. For example, multiple aptamers may bind to different regions of a single protein or peptide target simultaneously. The protein or peptide target may be large enough that the binding of one aptamer at one site does not significantly interfere with or prevent the simultaneous binding of a second antibody at a second site.

In some embodiments, an aptamer suitable for use with the methods and devices provided by the present disclosure can be developed using a multi-step process. In the first step of a multi-step development process, a first aptamer may be developed against a target, such as a microRNA, by any method described above. The first aptamer binds the target as a first aptamer:first target complex.

In a second or subsequent step of a multi-step process, a second aptamer may be developed against a second target, which may be the first aptamer:first target complex, by any method described above. The second aptamer may bind the second target as a second aptamer:(first aptamer:first target) complex (hereinafter, "second aptamer:second target").

In one embodiment, the first aptamer:first target complex created in the first step of a multi-step development process is treated in the second step as a new, distinct molecular entity for selecting a second aptamer. The second aptamer may be more selective for the first aptamer:first target complex than for the first target alone ("naked" first target).

For example, when the target is a microRNA, aptamers that bind a naked target microRNA may not bind the same target microRNA as well once the target microRNA is complexed with another aptamer. The target microRNA is typically a small molecule (for example, up to 80 nucleotides for precursors, and 21-23 nucleotides for mature species) that may not remain available for binding a second aptamer when already complexed with a first aptamer, such as due to steric hindrance by the first aptamer.

A multi-step aptamer development process may help produce aptamers that can be used in a multi-stage lateral flow assay (described in more detail below). Different stages of the assay may include separate and unique targets, and each developed aptamer may be specific to and selective for those separate and unique targets.

Development of Antibodies

In some embodiments, an associator is an antibody. One or more antibodies may be developed against one or more detection targets. Antibodies may be developed by any method known in the art, such as by synthesizing or purifying a target antigen, creating an immunogen comprising the target antigen, and immunizing an animal with the immunogen. Polyclonal antibodies may be recovered directly from serum of the immunized animal. Monoclonal antibodies may be produced by fusing spleen cells from the immunized animal with immortalized myeloma cells to create hybridoma cells lines that express the antibody. Antibody development may also include purification and characterization steps.

The presently disclosed antibodies may be developed in a single-step or multi-step process. In a single step process, antibodies are developed against a target, such as a microRNA, protein, or peptide. The antibody may bind the target as an antibody:target complex. Multiple antibodies may be developed against the same or different regions of a single target. When the target is of large enough size, such as a protein or peptide, the target may be bound simultaneously by more than one molecule at more than one site. For example, multiple antibodies may bind to different regions of a single protein or peptide target simultaneously. The protein or peptide target may be large enough that the binding of one antibody at one site does not significantly interfere with or prevent the simultaneous binding of a second antibody at a second site.

In the first step of a multi-step development process, a first antibody may be developed against a target, such as a microRNA. The first antibody binds the target as a first antibody:first target complex.

In a second or subsequent step of a multi-step process, a second antibody may be developed against a second target, which may be the first antibody:first target complex. The second antibody may bind the second target as a second antibody:(first antibody:first target) complex (hereinafter, "second antibody:second target").

In one embodiment, the first antibody:first target complex created in the first step of a multi-step development process is treated in the second step as a new, distinct molecular entity for selecting a second antibody. The second antibody may be more selective for the first antibody:first target complex than for the first target alone ("naked" first target).

For example, when the target is a microRNA, antibodies that bind a naked target microRNA may not bind the same target microRNA as well once the target microRNA is complexed with another antibody. The target microRNA is typically a small molecule (for example, up to 80 nucleotides for precursors, and 21-23 nucleotides for mature species) that may not remain available for binding a second antibody when already complexed with a first antibody, such as due to steric hindrance by the first antibody.

A multi-step antibody development process may help produce antibodies that can be used in a multi-stage lateral flow assay (described in more detail below). Different stages of the assay may include separate and unique targets, and each developed antibody may be specific to and selective for those separate and unique targets.

Components of Aptamer-Based Lateral Flow Device

In one embodiment, the presently disclosed assay to predict the initiation of parturition may be performed using a lateral flow device 100 as depicted in FIGS. 2A-2G.

In the embodiment depicted in FIGS. 2A-2G, the lateral flow device 100 includes a backing 102, membrane 104, sample pad 106, conjugate pad 108, capture pad 110, and absorbent pad 112. The backing 102 provides support for and/or a surface for attachment of the other components of the device 100. The membrane 104 may have wicking properties that help move fluids across or through the device 100. The absorbent pad 112 may collect fluid.

The sample pad 106 may be configured to receive a fluid sample 114. The sample 114 may be any bodily fluid such as urine, blood, saliva, plasma, amniotic fluid, and peritoneal fluid. The sample pad 106 may include a delay zone 116, which may comprise one or more delay reagents. One example of a delay reagent is a solution of a sugar, such as sucrose. The delay zone 116 controls the delivery of a sample 114 to another location on the device 100 by temporarily inhibiting, or reducing the rate of, the flow of fluid out of the delay zone 116. Varying the concentration or combination of delay reagents may vary the delay time. For example, increasing the concentration of a sucrose solution may increase the delay time. Delay reagents and delay zones 116 may be prepared according to the method disclosed by Lutz et al (Dissolvable Fluidic Time Delays For Automated Paper Diagnostics, 16th International Conference on Miniaturized Systems for Chemistry and Life Sciences, Oct. 28-Nov. 1, 2012, Okinawa, Japan, pages 788-790)

The delay zone 116 may also comprise one or more additional reagents such as a detergent. The detergent may be any detergent that is capable of lysing exosomes such as, for example, Triton™ X-100 (Dow Chemical), an octylphenol ethoxylate surfactant, nonylphenoxypolyethoxyethanol (NP-40), sodium dodecyl sulfate (SDS), cetyltrimethylammonium bromide (CTAB), and 3-[(3-cholamidopropyl)dimethylammonio]-1-propanesulfonate (CHAPS).

With continued reference to FIGS. 2A-2E, the conjugate pad 108 may include one or more first aptamers 120, each of which may be selective for a control target 118c or a first target-up 118a, which is a target that is up-regulated near the onset of parturition. Control targets 118c, such as microRNAs that may be involved in a housekeeping role in the cell or are otherwise regularly detectable, may include, but are not limited to, miR-22-3p, miR-99a-5p, miR-99b-5p, miR-124-3p, and miR-128. miR-128 may include mir-128-1, miR-128-1-5p, miR-128-1-3p, mir-128-2, miR-128-2-5p, and miR-128-2-3p. First targets-up 118a may include, but are not limited to, microRNAs such as miR-200a, miR-200b, and miR-429.

The first aptamers 120 may be immobilized on the conjugate pad 108, such as in a salt-sugar matrix. The matrix may facilitate binding of microRNAs to the first aptamers 120.

The first aptamers 120 may be conjugated to a molecule that will aid in detection, directly or indirectly, of the first aptamer:first target complexes 122. The molecules may include, but are not limited to, optical dyes, colored particles, fluorescent molecules, luminescent molecules, or phosphorescent molecules. For example, the first aptamers 120 may be conjugated to gold nanoparticles, latex, or biotin. A subset of first aptamers 120, such as those that bind first targets-up 118a (hereinafter, "first aptamer-up" 120a), may be conjugated to one reporter molecule and another subset of first aptamers 120, such as those that bind control targets 118c (hereinafter "first aptamer-control" 120c), may be conjugated to a different reporter molecule. For example, first aptamers-up 120a may be conjugated to gold nanoparticles, and first aptamers-control 120c may be conjugated to latex.

The capture pad 110 may comprise a test zone 124 and a control zone 126. The capture pad 110 may include one or more second aptamers 130, each of which may be selective for a first aptamer:first target complex 122. For example, a second aptamer 130 may be selective for the first aptamer:miR-200a complex. The second aptamers 130 may include a first subset that binds first aptamer:first target-up complexes 122a (hereinafter, "second aptamer-up" 130a). The second aptamers 130 may include another subset that binds first aptamer:control target complexes 122c (hereinafter, "second aptamer-control" 130c).

The second aptamers 130 may be immobilized on the capture pad 110, such as in a matrix. The matrix may facilitate binding of second aptamers 130 to first aptamer:first target complexes 122. The matrix may also help prevent the second aptamers 130 from migrating, even in the presence of a fluid. The matrix may be glass fibers.

The second aptamers 130 may be immobilized within the capture pad 110 in any arrangement or grouping. Various arrangements and groupings, in conjunction with the conjugation of first aptamers 120 to detectable molecules, may help produce a variety of assay result presentations. The assay results may indicate the proximity of the onset of labor or the proper functioning of the device 100 as described in more detail below.

In one embodiment, all second aptamers-up 130a may be immobilized at a location within the capture pad 110 that is distinct from the location of immobilization of all second aptamers-control 130c. For example, and with reference to FIGS. 2A-2E, second aptamers 130 that bind first aptamer:first target-up complexes 122a may be immobilized in a test zone 124. Second aptamers 130 that bind first aptamer:control target complexes 122c may be immobilized in a control zone 126.

Figure 2A:
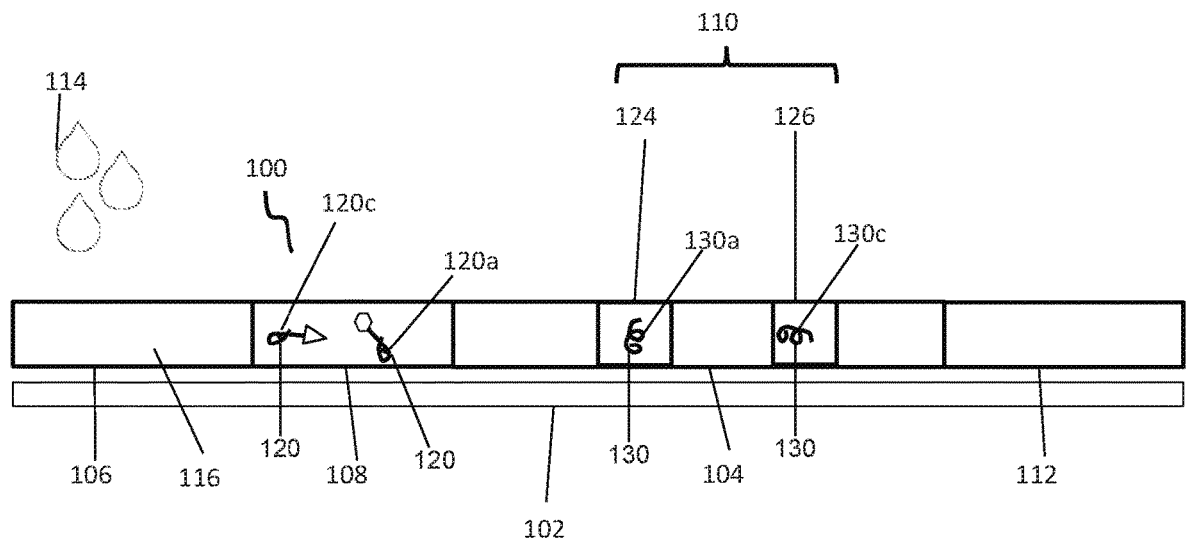
FIG. 2A is a schematic diagram of a lateral flow device according to one embodiment.
Figure 2B:
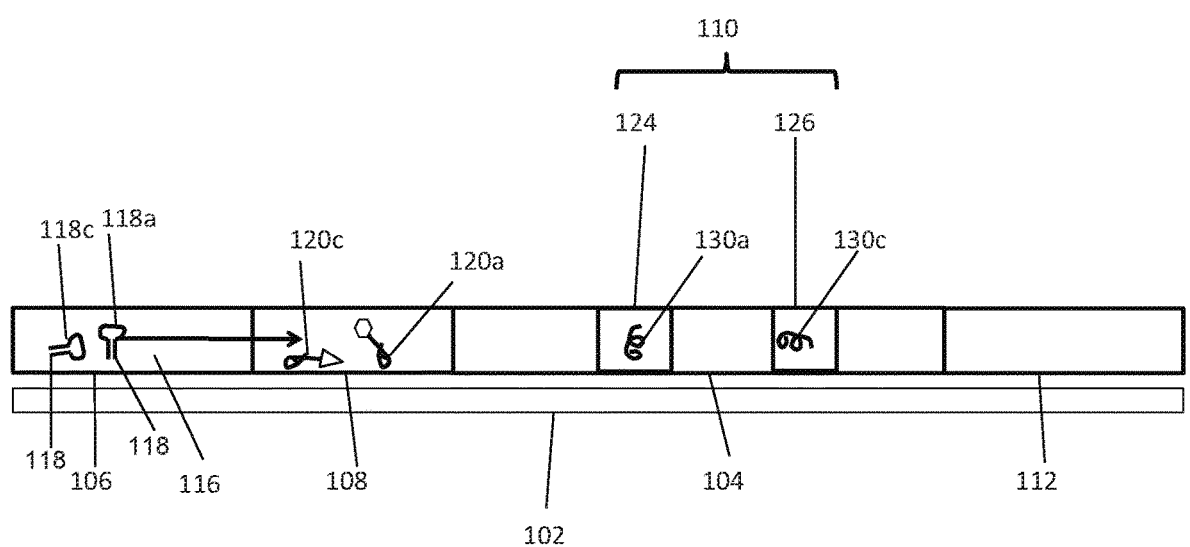
FIG. 2B is a schematic diagram of the lateral flow device of FIG. 2A after a sample has been applied.
Figure 2C:
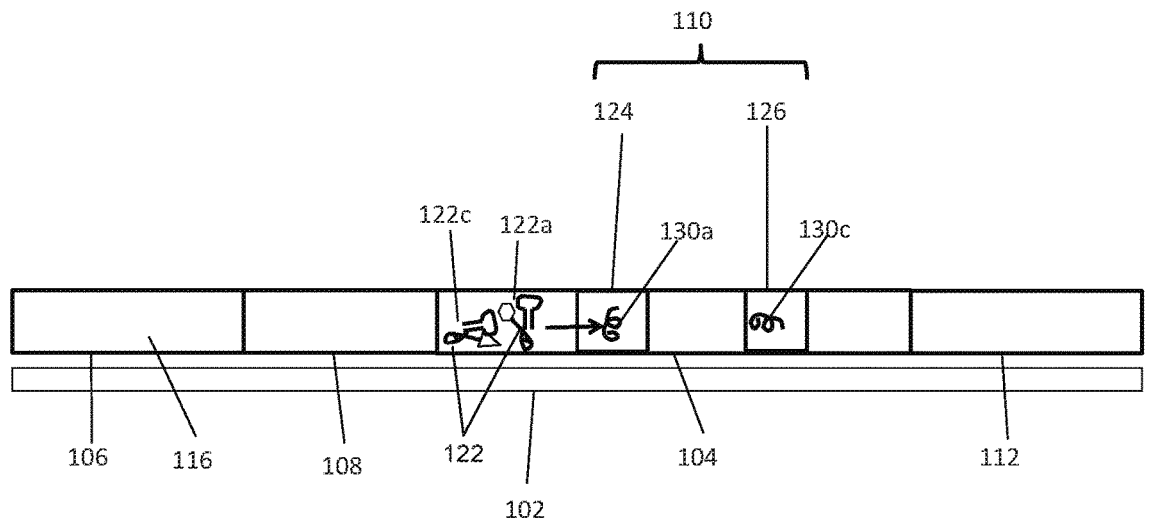
FIG. 2C is a schematic diagram of the lateral flow device of FIG. 2B after aptamer:target complexes have migrated along the device.
Figure 2D:
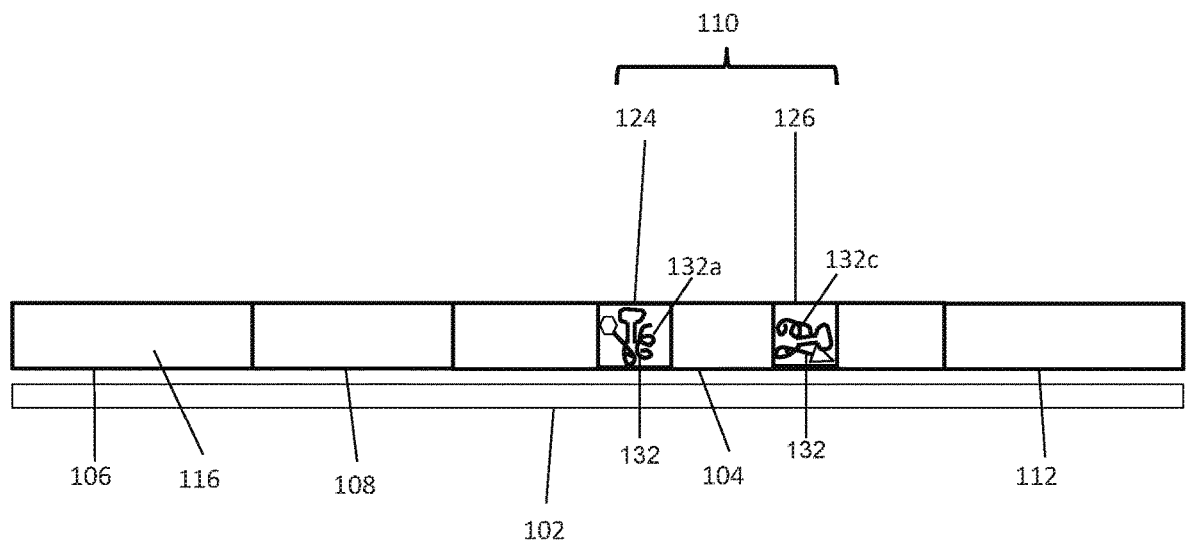
FIG. 2D is a schematic diagram of the lateral flow device of FIG. 2C after second aptamer:second target complexes have formed.
Figure 2E:
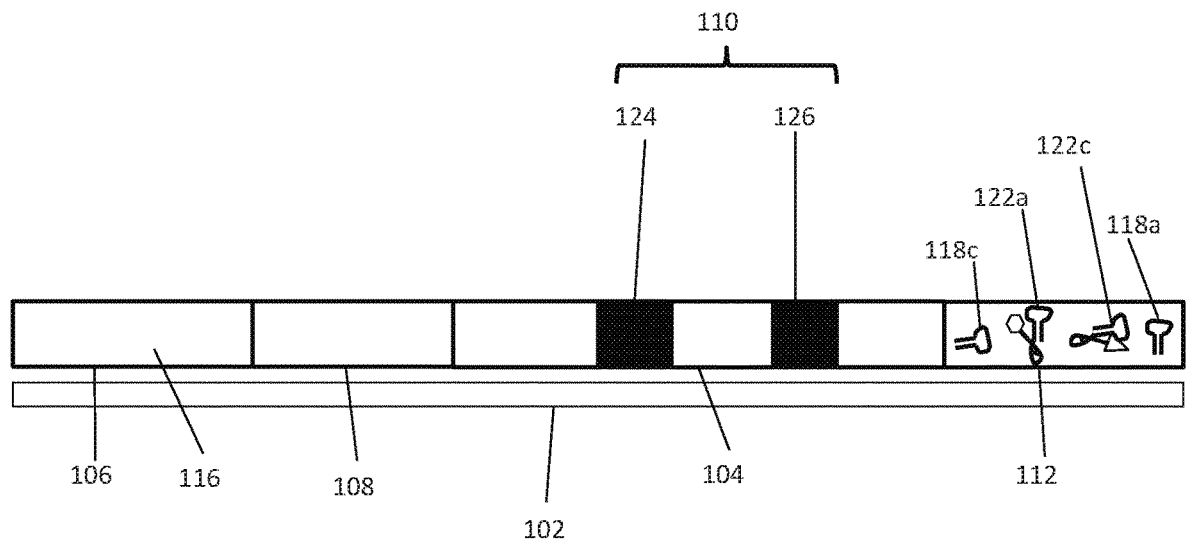
FIG. 2E is a schematic diagram of the lateral flow device of FIG. 2A showing test results according to one embodiment.
Figure 2F:
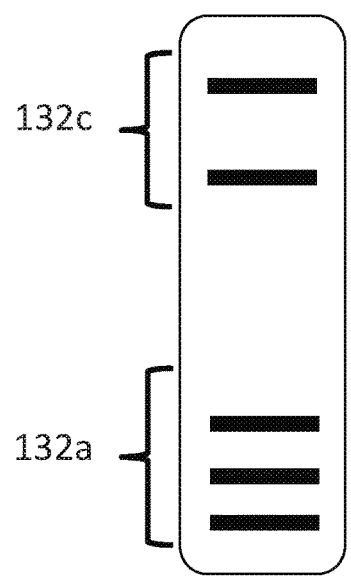
FIG. 2F is a partial schematic diagram of the lateral flow device of FIG. 2A showing test results according to another embodiment.
Figure 2G:
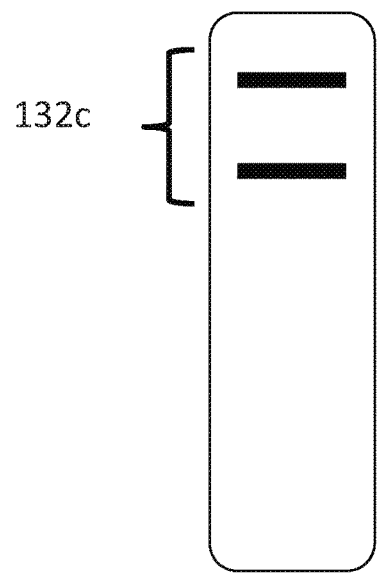
FIG. 2G is a partial schematic diagram of the lateral flow device of FIG. 2A showing test results according to another embodiment.

In another embodiment, and with reference to FIGS. 2F and 2G, each second aptamer 130 that binds a first aptamer:first target-up complex 122a may be immobilized separately. Each second aptamer 130 that binds a first aptamer:control target complex 122c may also be immobilized separately.

In one implementation, and with continued reference to FIGS. 2F and 2G, each second aptamer 130 may be immobilized in close proximity to the other second aptamers 130, such as in a single ladder-like pattern. For example, the second aptamers-up 130a and second aptamers-control 130c may be immobilized within a control pad 110. One line of the lower three-line ladder may represent the location at which the second-aptamer 130 specific for the first aptamer:miR-200a complex is immobilized, a second of the three lines may represent the location at which the second aptamer 130 specific for the first aptamer:miR-200b complex is immobilized, and the third line may represent the location at which the second aptamer 130 specific for the first aptamer:miR-429 complex is immobilized. One line of the upper two-line ladder may represent the location at which the second aptamer 130 specific for the first aptamer:miR-99a-5p complex is immobilized and the other of the lines may represent the location at which the second aptamer 130 specific for the first aptamer:miR-128 complex is immobilized.

In another implementation (not shown), the second aptamers-up 130a may be immobilized near each other, such as within the test zone 124. The second aptamers-control 130c may be immobilized near each other but at a location separate from the second aptamers-up 130a, such as within the control zone 126. Either or both of the subsets 130a, 130c of second aptamers 130 may be immobilized in ladder-like patterns. For example, the lower portion of FIG. 2F may represent the test zone 124 within which second aptamers-up 130a are immobilized. One of the three lines may represent the location at which the second aptamer 130 specific for the first aptamer:miR-200a complex is immobilized, a second of the three lines may represent the location at which the second-aptamer 130 specific for the first aptamer:miR-200b complex is immobilized, and the third line may represent the location at which the second-aptamer 130 specific for the first aptamer:miR-429 complex is immobilized. The upper portion of FIG. 2F may represent the control zone 126 within which second aptamers-control 130c are immobilized. One of the two lines may represent the location at which the second-aptamer 130 specific for the first aptamer:miR-99a-5p complex is immobilized and the other of the lines may represent the location at which the second-aptamer 130 specific for the first aptamer:miR-128 complex is immobilized.

The second aptamers 130 may be immobilized in any combination of the above arrangements. For example, all second aptamers-control 130c may be immobilized together as depicted in FIG. 2E and each second-aptamer-up 130a may immobilized separately as depicted in FIG. 2F.

In another embodiment, the presently disclosed assay to predict the initiation of parturition may be performed using a lateral flow device 100 as depicted in FIGS. 3A-3J. The backing 102, membrane 104, sample pad 106, conjugate pad 108, capture pad 110, absorbent pad 112, and delay zone 116 of the lateral flow device 100 are as described above for FIGS. 2A-2G.

The conjugate pad 108 of the embodiment depicted in FIGS. 3A-3J may include one or more first aptamers 120, each of which may be selective for a first target-up 118a or a first target-down 118b. First targets-up 118a may include, but are not limited to, microRNAs such as miR-200a, miR-200b, and miR-429. First targets-down 118b may include, but are not limited to, miR-199a-3p and miR-214.

The first aptamers 120 may be immobilized on the conjugate pad 108, such as in a salt-sugar matrix. The matrix may facilitate binding of microRNAs to the first aptamers 120.

The first aptamers 120 may be conjugated to a molecule that will aid in detection, directly or indirectly, of the first aptamer:first target complexes 122. The molecules may include, but are not limited to, optical dyes, colored particles, fluorescent molecules, luminescent molecules, or phosphorescent molecules. For example, the first aptamers 120 may be conjugated to gold nanoparticles, latex, or biotin. A subset of first aptamers 120, such as first aptamers-up 120a, may be conjugated to one reporter molecule and another subset of first aptamers 120, such as those that bind first targets-down 118b (hereinafter "first aptamer-down" 120b), may be conjugated to a different reporter molecule. For example, first aptamers-up 120a may be conjugated to gold nanoparticles, and first aptamers-down 120b may be conjugated to latex.

The capture pad 110 may comprise a test zone 124 and a control zone 126. The capture pad 110 may include one or more second aptamers 130, each of which may be selective for a first aptamer:first target complex 122. For example, a second aptamer 130 may be selective for the first aptamer: miR-200a complex. The second aptamers 130 may include a first subset that binds first aptamer:first target-up complexes 122a (second aptamer-up 130a). The second aptamers 130 may include another subset that binds first aptamer: first target-down complexes 122b (hereinafter, "second aptamer-down" 130b).

The second aptamers 130 may be immobilized on the capture pad 110, such as in a matrix. The matrix may facilitate binding of second aptamers 130 to first aptamer: first target complexes 122. The matrix may also help prevent the second aptamers 130 from migrating, even in the presence of a fluid. The matrix may be glass fibers.

The second aptamers 130 may be immobilized within the capture pad 110 in any arrangement or grouping. Various arrangements and groupings, in conjunction with the conjugation of first aptamers 120 to detectable molecules, may help produce a variety of assay result presentations. The assay results may indicate the proximity of the onset of labor or the proper functioning of the device 100 as described in more detail below.

In one embodiment, all second aptamers-up 130a may be immobilized at a location within the capture pad 110 that is distinct from the location of immobilization of all second aptamers-down 130b. For example, and with reference to FIGS. 3A-3G, second aptamers 130 that bind first aptamer: first target-up complexes 122a may be immobilized in a test zone 124. Second aptamers 130 that bind first aptamer:first target-down complexes 122b may be immobilized in a control zone 126.

Figure 3A:
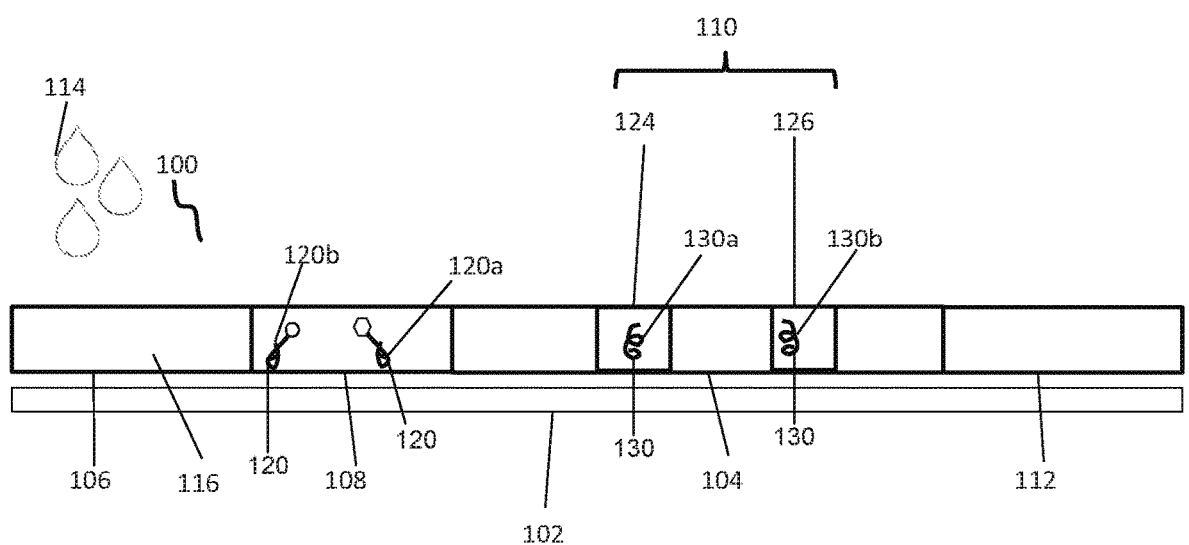
FIG. 3A is a schematic diagram of a lateral flow device according to another embodiment.
Figure 3B:
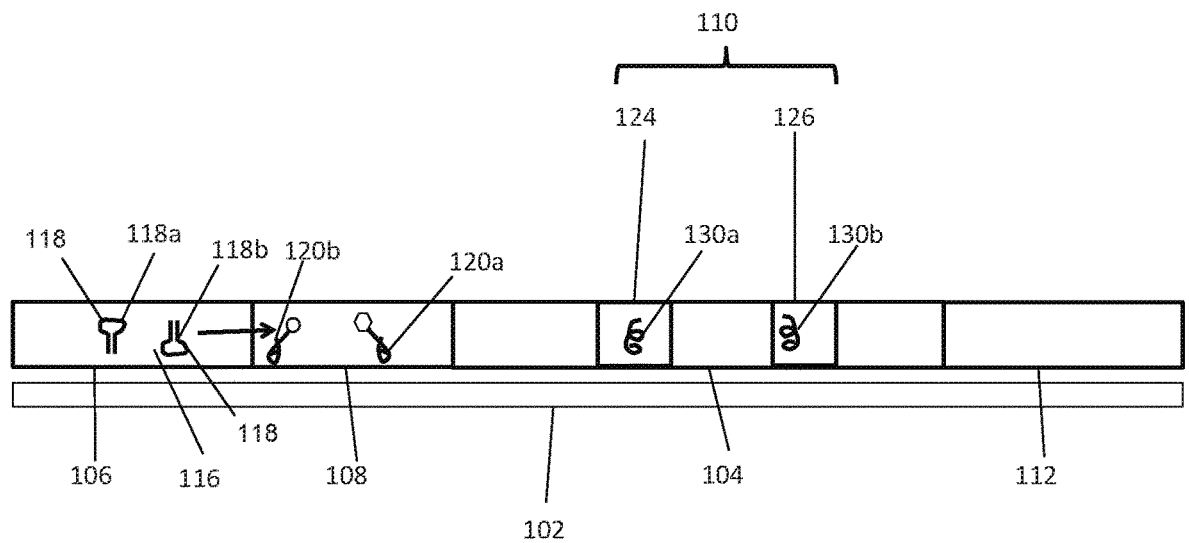
FIG. 3B is a schematic diagram of the lateral flow device of FIG. 3A after a sample has been applied.
Figure 3C:
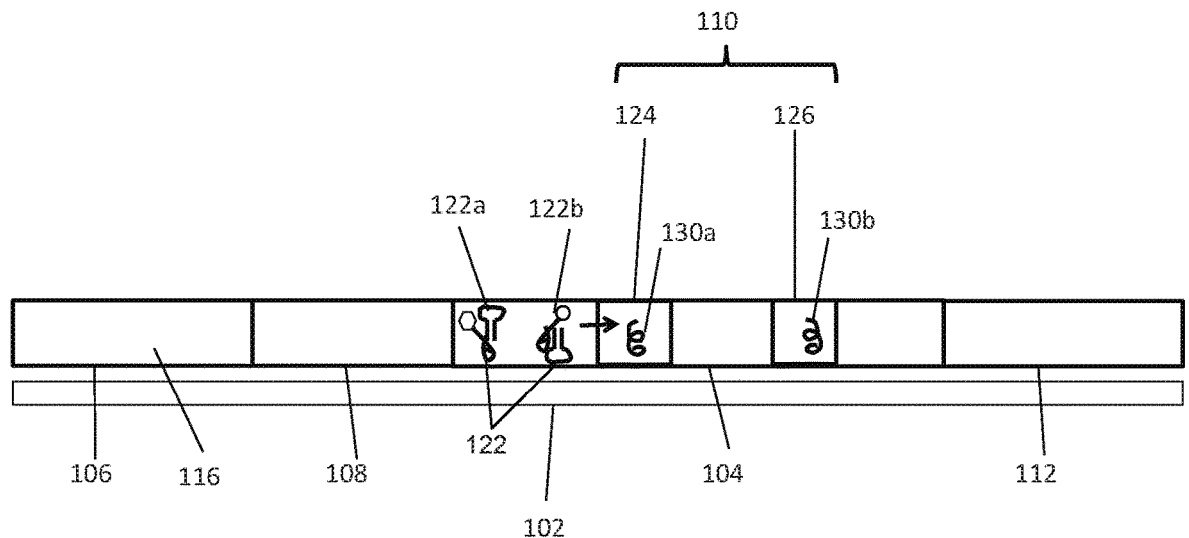
FIG. 3C is a schematic diagram of the lateral flow device of FIG. 3B after aptamer:target complexes have migrated along the device.
Figure 3D:
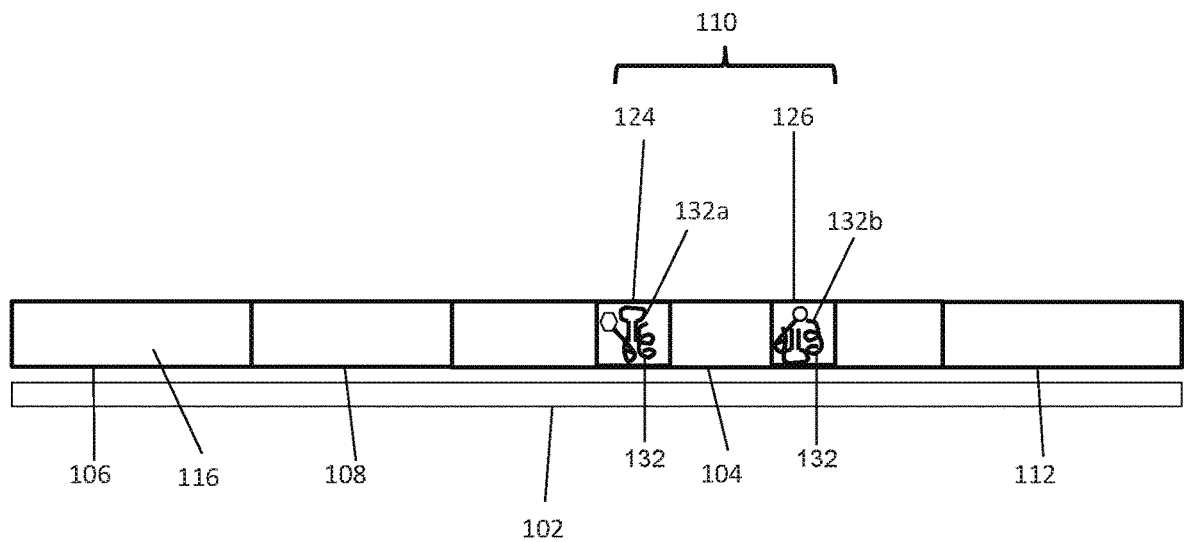
FIG. 3D is a schematic diagram of the lateral flow device of FIG. 3C after second aptamer:second target complexes have formed.
Figure 3E:
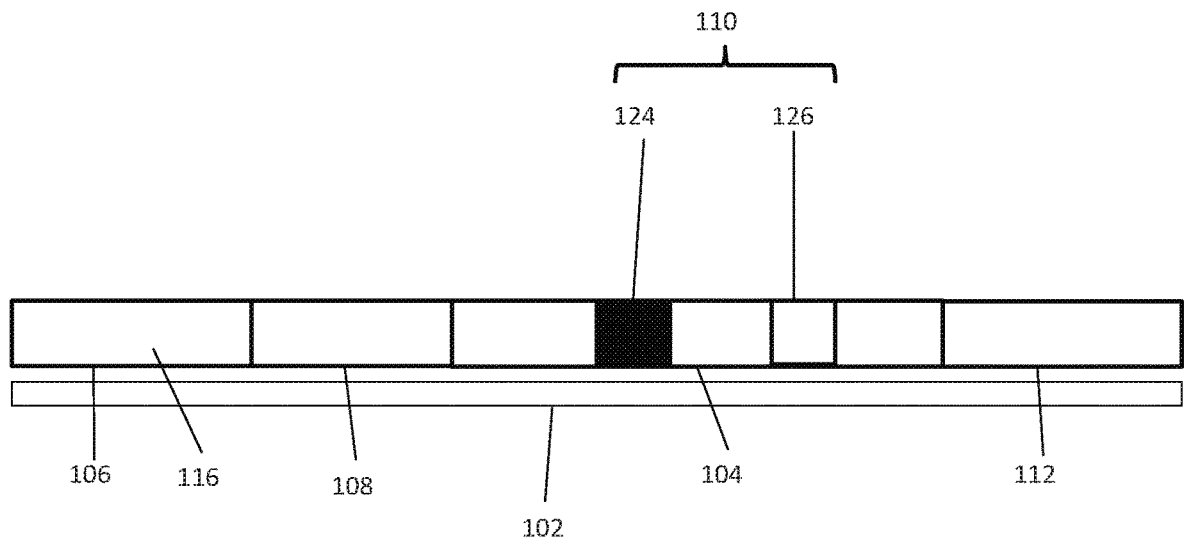
FIG. 3E is a schematic diagram of the lateral flow device of FIG. 3A showing test results according to one embodiment.
Figure 3F:
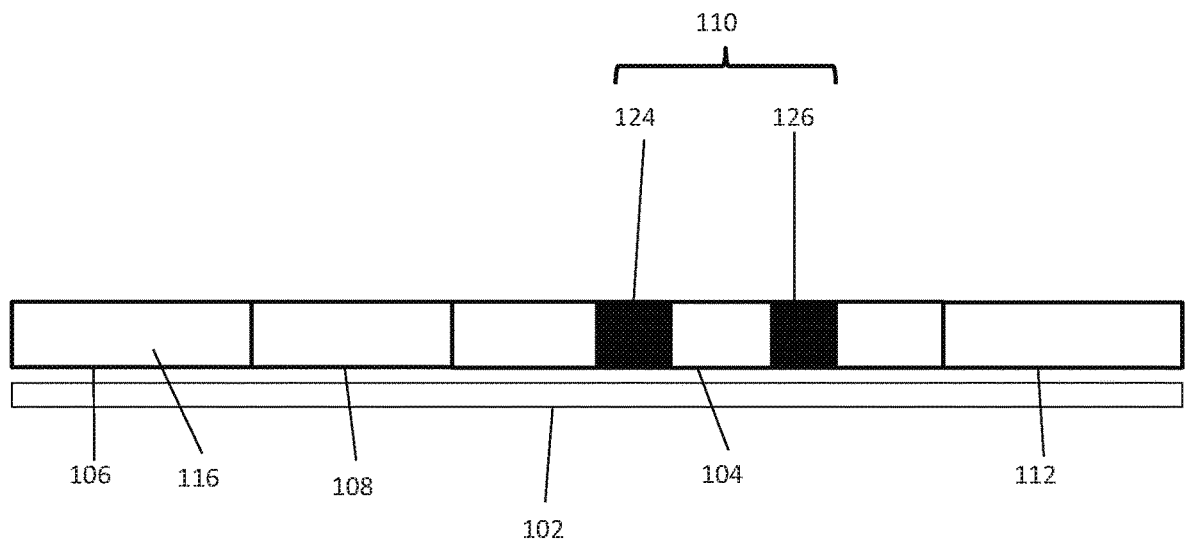
FIG. 3F is a schematic diagram of the lateral flow device of FIG. 3A showing test results according to another embodiment.
Figure 3G:
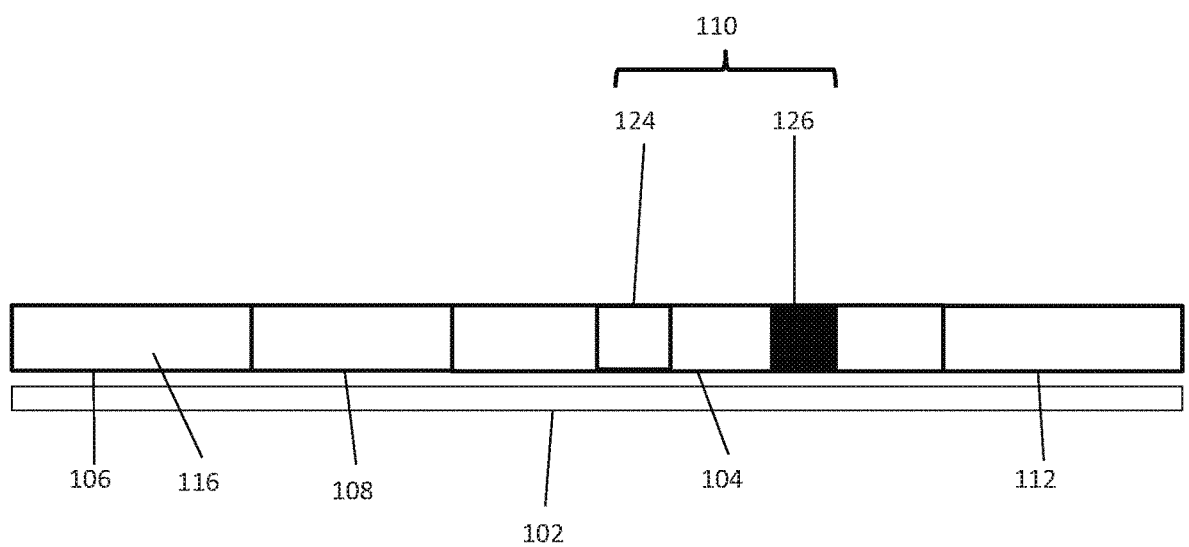
FIG. 3G is a schematic diagram of the lateral flow device of FIG. 3A showing test results according to another embodiment.
Figure 3H:
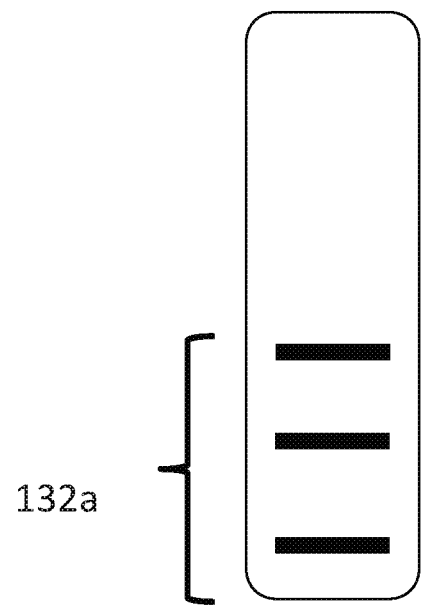
FIG. 3H is a partial schematic diagram of the lateral flow device of FIG. 3A showing test results according to another embodiment.
Figure 3I:
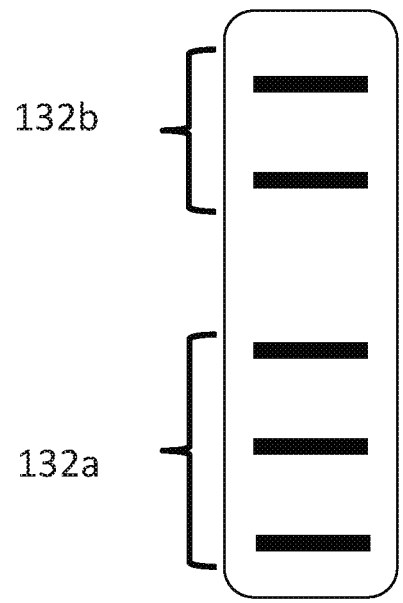
FIG. 3I is a partial schematic diagram of the lateral flow device of FIG. 3A showing test results according to another embodiment.
Figure 3J:
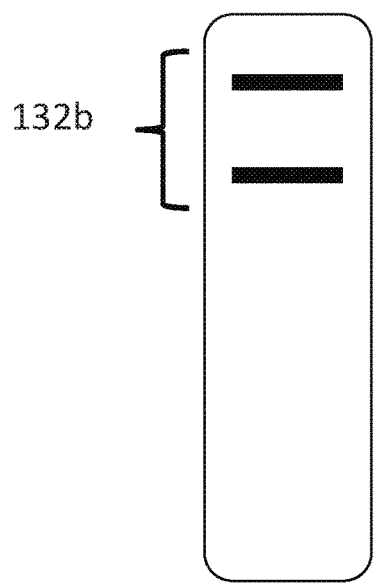
FIG. 3J is a partial schematic diagram of the lateral flow device of FIG. 3A showing test results according to another embodiment.

In another embodiment, and with reference to FIGS. 3H-3J, each second aptamer 130 that binds a first aptamer: first target-up complex 122a may be immobilized separately. Second aptamers 130 that bind first aptamer:first target-down complexes 122b may also be immobilized separately.

In one implementation, and with continued reference to FIGS. 3H-3J, each second aptamer 130 may be immobilized in close proximity to the other second aptamers 130, such as in a single ladder-like pattern. For example, the second aptamers-up 130a and second aptamers-down 130b may be immobilized within a capture pad 110. One line of the lower three-line ladder may represent the location at which the second-aptamer 130 specific for the first aptamer:miR-200a complex is immobilized, a second of the three lines may represent the location at which the second aptamer 130 specific for the first aptamer:miR-200b complex is immobilized, and the third line may represent the location at which the second aptamer 130 specific for the first aptamer: miR-429 complex is immobilized. One line of the upper two-line ladder may represent the location at which the second aptamer 130 specific for the first aptamer:miR-199a-3p complex is immobilized and the other of the lines may represent the location at which the second aptamer 130 specific for the first aptamer:miR-214 complex is immobilized.

In another implementation (not shown), the second aptamers-up 130a may be immobilized near each other, such as within the test zone 124. The second aptamers-down 130b may be immobilized near each other but at a location separate from the second aptamers-up 130a, such as within the control zone 126. Either or both of the subsets 130a, 130b of second aptamers 130 may be immobilized in ladder-like patterns. For example, the lower portion of FIG. 3I may represent the test zone 124 within which second aptamers-up 130a are immobilized. One of the three lines may represent the location at which the second aptamer 130 specific for the first aptamer:miR-200a complex is immobilized, a second of the three lines may represent the location at which the second-aptamer 130 specific for the first aptamer:miR-200b complex is immobilized, and the third line may represent the location at which the second-aptamer 130 specific for the first aptamer:miR-429 complex is immobilized. The upper portion of FIG. 3I may represent the control zone 126 within which second aptamers-down 130b are immobilized. One of the two lines may represent the location at which the second-aptamer 130 specific for the first aptamer:miR-199a-3p complex is immobilized and the other of the lines may represent the location at which the second-aptamer 130 specific for the first aptamer:miR-214 complex is immobilized.

The second aptamers 130 may be immobilized in any combination of the above arrangements. For example, all second aptamers-up 130a may be immobilized together as depicted in FIG. 3E-3G and each second-aptamer-down 130b may immobilized separately as depicted in FIGS. 3I and 3J.

Figure 4:
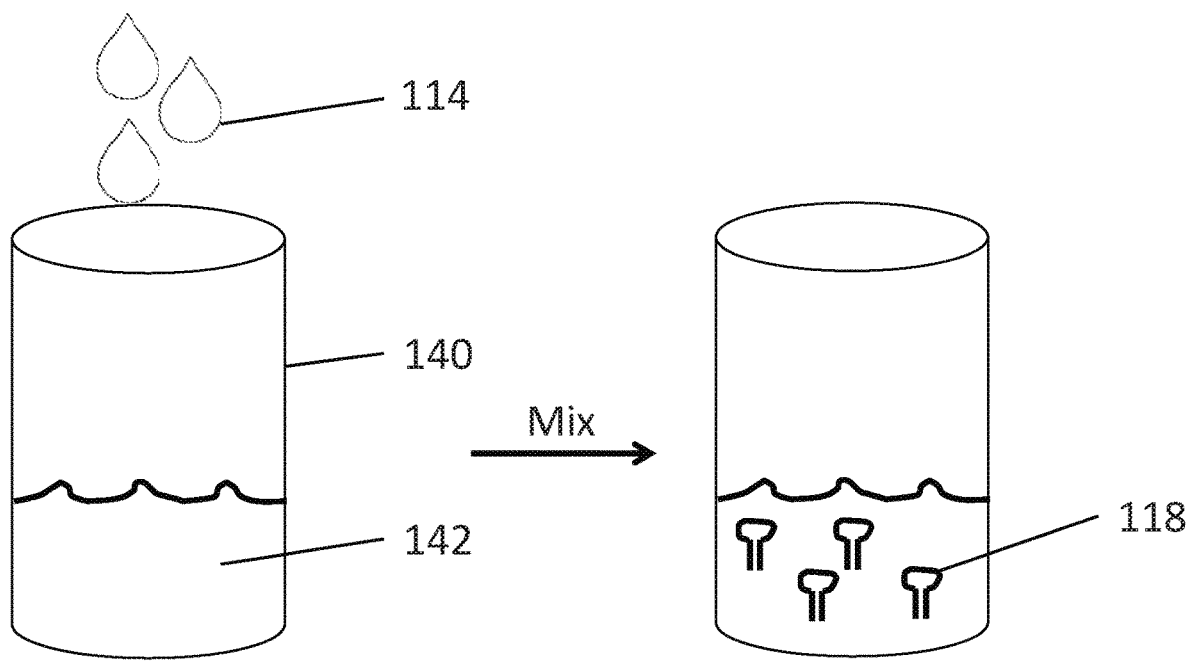
FIG. 4 is a schematic diagram of a lateral flow device according to another embodiment.

In another embodiment, and as shown in FIG. 4, the presently disclosed assay to predict the initiation of parturition may include a vessel 140 for exosome lysis separate from the lateral flow device 100 of FIGS. 2A-2G or 3A-3J. The vessel 140 may be any device suitable for receiving and mixing fluids, such as a cup, which may be a plastic cup. The vessel 140 may be configured to receive a detergent solution 142, which may include any one or more detergents capable of lysing exosomes, such as, for example, Triton™ X-100, NP-40, CTAB, and CHAPS. The vessel 140 may also be configured to receive a sample 114.

Incubation of a sample 114 with the detergent solution 142 in a vessel 140 may lyse exosomes in the sample 114 and liberate first targets 118, such as microRNAs. The sample pad 106 of the lateral flow devices 100 of FIGS. 2A-2G or 3A-3J may be configured to receive the detergent solution 142 with sample 114 comprising liberated first targets 118. In the present embodiment, the delay zones 116 of the sample pads 106 of FIGS. 2A-2G or 3A-3J may not include a detergent.

Operation of the Aptamer-Based Lateral Flow Devices

By way of example, but not limitation, the lateral flow device 100 FIGS. 2A-2G may operate according to the following procedure. When a fluid sample 114 is applied to the sample pad 106, the sample 114 is retained by a retaining agent or agents in the delay zone 116. While the sample 114 is in the delay zone 116, detergents embedded in the delay zone 116 lyse exosomes present in the sample 114 to yield liberated first targets 118, such as microRNAs. A sample 114 may be delayed in the delay zone 116 for a delay period of a few seconds to several minutes. For example, the delay period may be greater than 5 seconds, greater than 10 seconds, greater than 20 seconds, less than 5 minutes, less than 3 minutes, or less than 1 minute. The delay period may be 15-180 seconds. After the delay period, the sample 114, including liberated first targets 118, migrates via lateral (capillary) flow to the conjugate pad 108.

In the conjugate pad 108, the fluid sample 114 dissolves a matrix present in the conjugate pad, thereby releasing first aptamers 120 conjugated to reporter molecules. A subset of first aptamers 120, such as first aptamers-up 120a, is conjugated to one type of reporter molecule, such as gold nanoparticles. A second subset of first aptamers 120, such as first aptamers-control 120c, is conjugated to another type of reporter molecule, such as latex. The first aptamers 120 bind their first targets 118, if present, to form first aptamer:first target complexes 122. The first aptamer:first target complexes 122 may be first aptamer:first target-up complexes 122a. For example, a first aptamer 120 developed against miR-200a will bind miR-200a, if miR-200a is present in the sample 114, to form an aptamer:miR-200a complex. Other examples of first aptamer:first target-up complexes 122a include aptamer:miR-200b and aptamer:miR-429.

The first aptamer:first target complexes 122 may be first aptamer:first target-control 122c complexes. For example, a first aptamer 120 developed against miR-99a-5p will bind miR-99a-5p, if miR-99a-5p is present in the sample 114, to form an aptamer:miR-99a-5p complex. Other examples of first aptamer:first target-control complexes 122c include aptamer:miR-128.

The first aptamer:first target complexes 122 migrate via lateral flow through the conjugate pad 108 to the capture pad 110. In the capture pad 110, the second aptamers 130 bind their targets, if present, to form second aptamer:second target complexes 132.

The second aptamer:second target complexes 132 may be second aptamer:second target-up complexes 132a. For example, a second aptamer 130 developed against aptamer:miR-200a will bind aptamer:miR-200a, if aptamer:miR-200a is present, to form a second aptamer:(aptamer:miR-200a) complex. Other examples of second aptamer:second target-up complexes 132a include second aptamer:(aptamer:miR-200b) and second aptamer:(aptamer:miR-429).

The second aptamer:second target complexes 132 may be second aptamer:second target-control 132c complexes. For example, a second aptamer 130 developed against aptamer:miR-99a-5p will bind aptamer:miR-99a-5p, if aptamer:miR-99a-5p is present, to form a second aptamer:(aptamer:miR-99a-5p) complex. Other examples of second aptamer:second target-control complexes 132c include second aptamer:(aptamer:miR-128).

The second aptamer:second target complexes 132 may remain stationary on the capture pad 110 at the area of immobilization of the respective second aptamers 130. The accumulation of multiple second aptamer:second target complexes 132 may result in a detectable signal. Without being limited to any mechanism or mode of action, the detectable signal may be the product of the presence of multiple reporter molecules that are conjugated to the first aptamers 120. In some embodiments, the signal is detectable with the human eye. In some embodiments, the signal is detectable with a densitometer, a fluorometer, a luminometer, or a phosphorimeter. The shape of the signal may be dependent on the arrangement of the immobilized second aptamers 130. The signal may be in the shape of a single line or multiple lines, such as a plus sign.

In the embodiment depicted in FIG. 2E, one signal is produced for all second aptamer:second target-up complexes 132a, if present. A separate signal is produced for all second aptamer:second target-control complexes 132c, if present. In some embodiments, the signals are distinct from each other, such as different visibly detectable colors. For example, first aptamers-up 120a may be conjugated to gold nanoparticles, and the accumulation of second aptamer:second target-up complexes 132a may yield a visibly detectable red line. As another example, first aptamers-control 120c may be conjugated to latex, and the accumulation of second aptamer:second target-control complexes 132c may yield a visibly detectable blue line. In some embodiments, the first aptamers-up 120a and first aptamers-control 120b may be conjugated to the same type of reporter molecule, such as gold nanoparticles, and the accumulation of either second aptamer:second target-up complexes 132a or second aptamer:second target-control complexes 120b, or both, may yield visibly detectable red lines.

The signals may convey assay results. For example, as depicted in FIG. 2E, a signal at the test zone 124 may indicate that at least one first target-up 118a is present in the sample 114. A signal at the control zone 126 may indicate that at least one first target-control 118c is present in the sample 114.

In one embodiment, and as shown in FIG. 2E, binary results may be produced. The presence of a signal in the test zone 124 may indicate that the initiation of parturition is near. The absence of a signal in the test zone 124 (not shown) may indicate that the initiation of parturition is not near. Without being limited to any mechanism of mode of action, the result depicted in FIG. 2E may indicate that parturition is near because the parturition signaling cascade has led to an increase in first targets up 118a to levels detectable in the sample 114. The absence of a signal in the test zone 124 (not shown) may indicate that the initiation of parturition is not near because the first targets up 118a are not yet at detectable levels in the sample 114.

Binary assay results may indicate a specific timeframe for the onset of parturition. For example, the presence of a signal in the test zone 124 may indicate that parturition will initiate within a certain number of hours. The number of hours may be 6 or less, 12 or less, 24 or less, 36 or less, 48 or less, 60 or less, 72 or less, 84 or less, or 96 or less. As another example, the absence of a signal in the test zone 124 may indicate that parturition will not initiate within a certain number of hours. The number of hours may be 96 or less, 84 or less, 72 or less, 60 or less, 48 or less, 36 or less, 24 or less, 12 or less, or 6 or less.

Returning to the production of signals, in the embodiment depicted in FIGS. 2F and 2G, a separate signal is produced for each second aptamer:second target-up complex 132a that is present and for each second aptamer:second target-control complex 132c that is present. In one embodiment, each signal is both separate and distinct from every other signal, such as each signal having a different visibly detectable color. In another embodiment, each signal may be separate but not distinct, such as each second aptamer:second target-up complex 132a yielding a red line and each second aptamer:second target-control complex 132b yielding a blue line.

With reference to FIG. 2F, the presence of one or more signals indicating the presence of one or more first targets-up 118a may indicate that the initiation of parturition is near. With reference to FIG. 2G, the presence of one or more signals indicating the presence of one or more first targets-control 118c and the absence of any signals indicating the presence of at least one first target-up 118a may indicate that the initiation of parturition is not near. Without being limited to any mechanism of mode of action, the result depicted in FIG. 2F may indicate that parturition is near because the parturition signaling cascade has led to an increase in at least one first target-up 118a to a level detectable in the sample 114. The result depicted in FIG. 2G may indicate that parturition is not near because no first targets up 118a are detectable yet in the sample 114.

The design of the lateral flow device 100 may affect the meaning of the assay results depicted in any of FIGS. 2E-2G. For example, first aptamers 120 specific for first targets-up 118a that are up-regulated early in the parturition signaling cascade may be included in the device 100. Alternatively, or additionally, first aptamers 120 specific for first targets-up 118a that are up-regulated later in the parturition cascade may be included in the device 100. In one example, a first aptamer 120 specific for the first target-up 118a that is the first to be up-regulated in the cascade is included in the device 100 (as is the corresponding second aptamer 130 specific for the first aptamer:first target-up complex 122a), and a signal indicating the presence of the first target-up 118a indicates that the initiation of parturition is, for example, 96 hours or less away. In another example, a first aptamer 120 specific for the first target-up 118a that is the last to be up-regulated in the cascade is included in the device 100 (as is the corresponding second aptamer 130 specific for the first aptamer:first target-up complex 122a), and a signal indicating the presence of the first target-up 118a indicates that the initiation of parturition is less than 96 hours or less away, such as 6 hours or less away.

With reference to FIGS. 2E-2G, the absence of any signal may indicate that no or too few first targets 118 were present in the sample 114, or that the lateral flow device 100 did not operate as designed.

By way of example, but not limitation, the lateral flow device 100 of FIGS. 3A-3J may operate according to the following procedure. First targets 118 migrate toward a conjugate pad 108 after being liberated from a sample 114 that has been applied to a sample pad 106 according to the procedure described above for FIGS. 2A-2G.

In the conjugate pad 108, the fluid sample 114 dissolves a matrix present in the conjugate pad, thereby releasing first aptamers 120 conjugated to reporter molecules. A subset of first aptamers 120, such as first aptamers-up 120a, is conjugated to one type of reporter molecule, such as gold nanoparticles. A second subset of first aptamers 120, such as first aptamers-down 120b, is conjugated to another type of reporter molecule, such as latex. The first aptamers 120 bind their first targets 118, if present, to form first aptamer:first target complexes 122. The first aptamer:first target complexes 122 may be first aptamer:first target-up complexes 122a. For example, a first aptamer 120 developed against miR-200a will bind miR-200a, if miR-200a is present in the sample 114, to form an aptamer:miR-200a complex. Other examples of first aptamer:first target-up complexes 122a include aptamer:miR-200b and aptamer:miR-429.

The first aptamer:first target complexes 122 may be first aptamer:first target-down 122b complexes. For example, a first aptamer 120 developed against miR-199a-3p will bind miR-199a-3p, if miR-199a-3p is present in the sample 114, to form an aptamer:miR-199a-3p complex. Other examples of first aptamer:first target-down complexes 122b include aptamer:miR-214.

The first aptamer:first target complexes 122 migrate via lateral flow through the conjugate pad 108 to the capture pad 110. In the capture pad 110, the second aptamers 130 bind their targets, if present, to form second aptamer:second target complexes 132.

The second aptamer:second target complexes 132 may be second aptamer:second target-up complexes 132a. For example, a second aptamer 130 developed against aptamer:miR-200a will bind aptamer:miR-200a, if aptamer:miR-200a is present, to form a second aptamer:(aptamer:miR-200a) complex. Other examples of second aptamer:second target-up complexes 132a include second aptamer:(aptamer:miR-200b) and second aptamer:(aptamer:miR-429).

The second aptamer:second target complexes 132 may be second aptamer:second target-down 132b complexes. For example, a second aptamer 130 developed against aptamer:miR-199a-3p will bind aptamer:miR-199a-3p, if aptamer:miR-199a-3p is present, to form a second aptamer:(aptamer:miR-199a-3p) complex. Other examples of second aptamer:second target-down complexes 132b include second aptamer:(aptamer:miR-214).

The second aptamer:second target complexes 132 may remain stationary on the capture pad 110 at the area of immobilization of the respective second aptamers 130. The accumulation of multiple second aptamer:second target complexes 132 may result in a detectable signal. Without being limited to any mechanism or mode of action, the detectable signal may be the product of the presence of multiple reporter molecules that are conjugated to the first aptamers 120. In some embodiments, the signal is detectable with the human eye. In some embodiments, the signal is detectable with a densitometer, a fluorometer, a luminometer, or a phosphorimeter. The shape of the signal may be dependent on the arrangement of the immobilized second aptamers 130. The signal may be in the shape of a single line or multiple lines, such as a plus sign.

In the embodiments depicted in FIGS. 3E-3G, one signal is produced for all second aptamer:second target-up complexes 132a, if present. A separate signal is produced for all second aptamer:second target-down complexes 132b, if present. In some embodiments, the signals are distinct from each other, such as different visibly detectable colors. For example, first aptamers-up 120a may be conjugated to gold nanoparticles, and the accumulation of second aptamer:second target-up complexes 132a may yield a visibly detectable red line. As another example, first aptamers-down 120b may be conjugated to latex, and the accumulation of second aptamer:second target-down complexes 132b may yield a visibly detectable blue line. In some embodiments, the first aptamers-up 120a and first aptamers-down 120b may be conjugated to the same type of reporter molecule, such as gold nanoparticles, and the accumulation of either second aptamer:second target-up complexes 132a or second aptamer:second target-down complexes 120b, or both, may yield visibly detectable red lines.

The signals may convey assay results. For example, as depicted in FIGS. 3E-3G, a signal at the test zone 124 may indicate that at least one first target-up 118a is present in the sample 114. A signal at the control zone 126 may indicate that at least one first target-down 118b is present in the sample 114.

In one embodiment, and as shown in FIGS. 3E and 3G, binary results may be produced. With reference to FIG. 3E, the presence of a signal in the test zone 124 and the absence of a signal in the control zone 126 may indicate that the initiation of parturition is near. With reference to FIG. 3G, the presence of a signal in the control zone 126 and the absence of a signal in the test zone 124 may indicate that the initiation of parturition is not near. Without being limited to any mechanism of mode of action, the result depicted in FIG. 3E may indicate that parturition is near because the parturition signaling cascade has led to an increase in first targets up 118a to levels detectable in the sample 114 and to a decrease in first targets-down 118b to levels not detectable in the sample 114. The result depicted in FIG. 3G may indicate that parturition is not near because the first targets-down 118b are still at levels high enough to be detectable in the sample 114, and the first targets up 118a are not yet at detectable levels in the sample 114.

Another example of binary results is shown in FIG. 3F. The presence of a signal in the test zone 124 and the presence of a signal in the control zone 126 may indicate that the initiation of parturition is near. Without being limited to any mechanism of mode of action, the result depicted in FIG. 3F may indicate that parturition is near because the parturition signaling cascade has led to an increase in first targets up 118a to levels detectable in the sample 114, even though it has not yet led to a decrease in first targets-down 118b to levels below a detectable threshold in the sample 114. The simultaneous detection of both first targets-up 118a and first targets-down 118b may occur when the device 100 includes first aptamers 120 that are specific to first targets-up 118a, the up-regulation of which precedes the down-regulation of the first targets-down 118b for which specific first aptamers 120 have been also included. The simultaneous detection may also occur when the device 100 includes first aptamers 120 that are specific to first targets-up 118a and to first targets-down 118b that are up- and down-regulated, respectively, relatively simultaneously, but the sample 114 was taken at a time point in the cascade when first targets-down 118b are still present at detectable levels.

Binary assay results may indicate a specific timeframe for the onset of parturition. For example, the presence of a signal in the test zone 124 and either the presence (FIG. 3F) or the absence (FIG. 3E) of a signal in the control zone 126 may indicate that parturition will initiate within a certain number of hours. The number of hours may be 6 or less, 12 or less, 24 or less, 36 or less, 48 or less, 60 or less, 72 or less, 84 or less, or 96 or less. As another example, and with reference again to FIG. 3G, the presence of a signal in the control zone 126 and the absence of a signal in the test zone 124 may indicate that parturition will not initiate within a certain number of hours. The number of hours may be 96 or less, 84 or less, 72 or less, 60 or less, 48 or less, 36 or less, 24 or less, 12 or less, or 6 or less.

The number of hours until initiation or no initiation of parturition may be the same or different. For example, a sample 114 from a pregnant woman applied to one unit of the device 100 may produce either the results as shown in FIG. 3E or 3F or the results as shown in FIG. 3G. In one embodiment, the results shown in FIG. 3E or 3F may indicate that the pregnant woman from whom the sample 114 was taken will go into labor within, for example, 48 hours of the time the sample 114 was taken, and results as shown in FIG. 3G may indicate that the woman will not go into labor within 48 hours. In another embodiment, the results shown in FIG. 3E or 3F may indicate that the woman from whom the sample 114 was taken will go into labor within, for example, 48 hours of the time the sample 114 was taken, and results as shown in FIG. 3G may indicate that the woman will not go into labor within, for example, 72 hours.

In another embodiment, the results depicted in FIG. 3F may represent a range, or window, of time until the initiation of parturition. The range may be 6-12, 6-24, 6-36, 6-48, 6-60, 6-72, 6-84, 6-96, 12-24, 12-36, 12-48, 12-60, 12-72, 12-84, 12-96, 24-36, 24-48, 24-60, 24-72, 24-84, 24-96, 36-48, 36-60, 36-72, 36-84, 36-96, 48-60, 48-72, 48-84, 48-96, 60-72, 60-84, 60-96, 72-84, 72-96, or 84-96 hours. A sample 114 from a pregnant woman applied to one unit of the device 100 may produce the results as shown in FIG. 3E, 3F, or FIG. 3G. The results as shown in FIG. 3E may indicate that the pregnant woman from whom the sample 114 was taken will go into labor within, for example, 24 hours of the time the sample 114 was taken, the results as shown in FIG. 3F may indicate that the woman will go into labor within, for example, 24-72 hours, and the results as shown in FIG. 3G may indicate that the woman will not go into labor within, for example, 72 hours.

Returning to the production of signals, in the embodiment depicted in FIGS. 3H-3J, a separate signal is produced for each second aptamer:second target-up complex 132a that is present and for each second aptamer:second target-down complex 132b that is present. In one embodiment, each signal is both separate and distinct from every other signal, such as each signal having a different visibly detectable color. In another embodiment, each signal may be separate but not distinct, such as each second aptamer:second target-up complex 132a yielding a red line and each second aptamer:second target-down complex 132b yielding a blue line.

With reference to FIG. 3H, the presence of one or more signals indicating the presence of one or more first targets-up 118a and the absence of any signals indicating the presence of at least one first target-down 118b may indicate that the initiation of parturition is near. With reference to FIG. 3J, the presence of one or more signals indicating the presence of one or more first targets-down 118b and the absence of any signals indicating the presence of at least one first target-up 118a may indicate that the initiation of parturition is not near. Without being limited to any mechanism of mode of action, the result depicted in FIG. 3H may indicate that parturition is near because the parturition signaling cascade has led to an increase in at least one first target-up 118a to a level detectable in the sample 114 and to a decrease in first targets-down 118b to levels not detectable in the sample 114. The result depicted in FIG. 3J may indicate that parturition is not near because the first targets-down 118b are still at levels high enough to be detectable in the sample 114, and no first targets up 118a are detectable yet in the sample 114.

In another implementation, and with reference to FIG. 3I, the presence of one or more signals indicating the presence of one or more first targets-up 118a and the presence of one or more signals indicating the presence of at least one first target-down 118b may indicate that the initiation of parturition is near. Without being limited to any mechanism of mode of action, the result depicted in FIG. 3I may indicate that parturition is near because the parturition signaling cascade has led to an increase in at least one first target-up 118a to a level detectable in the sample 114, even though it has not yet led to a decrease in all first targets-down 118b to levels below a detectable threshold in the sample 114. The simultaneous detection of both first targets-up 118a and first targets-down 118b may occur when the device 100 includes first aptamers 120 that are specific to first targets-up 118a, the up-regulation of which precedes the down-regulation of the first targets-down 118b for which specific first aptamers 120 have been also included. The simultaneous detection may also occur when the device 100 includes first aptamers 120 that are specific to first targets-up 118a and to first targets-down 118b that are up- and down-regulated, respectively, relatively simultaneously, but the sample 114 was taken at a time point in the cascade when first targets-down 118b are still present at detectable levels.

The assay results of FIGS. 3H-3J may indicate a specific timeframe for the onset of parturition. For example, the presence of one or more signals indicating the presence of one or more first targets-up 118a, with (FIG. 3I) or without (FIG. 3H) the presence of one or more signals indicating the presence of one or more first targets-down 118b, may indicate that parturition will initiate within a certain number of hours. The number of hours may be 6 or less, 12 or less, 24 or less, 36 or less, 48 or less, 60 or less, 72 or less, 84 or less, or 96 or less. As another example, and with reference again to FIG. 3J, the presence of one or more signals indicating the presence of one or more first targets-down 118b and the absence of any signals indicating the presence of at least one first target-up 118a may indicate that parturition will not initiate within a certain number of hours. The number of hours may be 96 or less, 84 or less, 72 or less, 60 or less, 48 or less, 36 or less, 24 or less, 12 or less, or 6 or less.

The number of hours until initiation or no initiation of parturition may be the same or different. For example, a sample 114 from a pregnant woman applied to one unit of the device 100 may produce either the results as shown in FIG. 3H or 3I or the results as shown in FIG. 3J. In one embodiment, the results shown in FIG. 3H or 3I may indicate that the pregnant woman from whom the sample 114 was taken will go into labor within, for example, 48 hours of the time the sample 114 was taken, and results as shown in FIG. 3J may indicate that the woman will not go into labor within 48 hours. In another embodiment, the results shown in FIG. 3H or 3I may indicate that the woman from whom the sample 114 was taken will go into labor within, for example, 48 hours of the time the sample 114 was taken, and results as shown in FIG. 3J may indicate that the woman will not go into labor within, for example, 72 hours.

In another embodiment, the results depicted in FIG. 3I may represent a range, or window, of time until the initiation of parturition. The range may be 6-12, 6-24, 6-36, 6-48, 6-60, 6-72, 6-84, 6-96, 12-24, 12-36, 12-48, 12-60, 12-72, 12-84, 12-96, 24-36, 24-48, 24-60, 24-72, 24-84, 24-96, 36-48, 36-60, 36-72, 36-84, 36-96, 48-60, 48-72, 48-84, 48-96, 60-72, 60-84, 60-96, 72-84, 72-96, or 84-96 hours. A sample 114 from a pregnant woman applied to one unit of the device 100 may produce the results as shown in FIG. 3H, 3I, or FIG. 3J. The results as shown in FIG. 3H may indicate that the pregnant woman from whom the sample 114 was taken will go into labor within, for example, 24 hours of the time the sample 114 was taken, the results as shown in FIG. 3I may indicate that the woman will go into labor within, for example, 24-72 hours, and the results as shown in FIG. 3J may indicate that the woman will not go into labor within, for example, 72 hours.

The design of the lateral flow device 100 may affect the significance of the assay results depicted in any of FIGS. 3E-3J. For example, first aptamers 120 specific for first targets-up 118a that are up-regulated early in the parturition signaling cascade may be included in the device 100. Alternatively, or additionally, first aptamers 120 specific for first targets-up 118a that are up-regulated later in the parturition cascade may be included in the device 100. First aptamers 120 specific for first targets-down 118b that are down-regulated early in the parturition signaling cascade may be included. Alternatively, or additionally, first aptamers 120 specific for first targets-down 118b that are down-regulated late in the cascade may be included. In one example, a first aptamer 120 specific for the first target-up 118a that is the first to be up-regulated in the cascade is included in the device 100 (as is the corresponding second aptamer 130 specific for the first aptamer:first target-up complex 122a), and a signal indicating the presence of the first target-up 118a indicates that the initiation of parturition is, for example, 96 hours or less away. In another example, a first aptamer 120 specific for the first target-up 118a that is the last to be up-regulated in the cascade is included in the device 100 (as is the corresponding second aptamer 130 specific for the first aptamer:first target-up complex 122a), and a signal indicating the presence of the first target-up 118a indicates that the initiation of parturition is less than 96 hours or less away, such as 6 hours or less away.

With reference to FIGS. 3E-3J, the absence of any signal may indicate that no or too few first targets 118 were present in the sample 114, or that the lateral flow device 100 did not operate as designed.

By way of example, but not limitation, the vessel 140 of FIG. 4 may operate according to the following procedure. Detergent solution 142 and sample 114 are mixed and incubated in the vessel 140. During incubation, the detergent solution 142 may lyse exosomes present in the sample 114 and release the exosome contents, such as first targets 118, which may be microRNAs. The detergent solution 142 with sample 114 may be applied to the sample pad 106 of the lateral flow device 100 of FIGS. 2A-2G or 3A-3J. When used in conjunction with the vessel 140 of FIG. 4, the delay zones 116 of the sample pads 106 of FIGS. 2A-2G or 3A-3J may not include a detergent.

Methods of Use of the Aptamer-Based Lateral Flow Devices

By way of example, but not limitation, the lateral flow device 100 of FIGS. 2A-2G may be used to determine the onset of parturition according to the following procedure.

The assay may be performed in a private setting, such as in a home, or in a medical environment, such as a doctor's office. The assay may be conducted by a pregnant woman using her own sample (described below), by non-medical personnel assisting a pregnant woman, or by medical personnel.

A sample 114 is applied to the lateral flow device 100. The sample 114 may be applied dropwise, by submerging the device in the sample 114, or by otherwise contacting the device with the sample 114. When the sample 114 is urine, the sample 114 may be applied to the device 100 by urinating directly on the device 100.

Following application of a sample 114, the user may not need to provide any input to the lateral flow device 100. The user may wait a predetermined amount of time until results are available. Results may be available in 1-20 minutes, 1-10 minutes, 1-5 minutes, 1-3 minutes, or less than 5 minutes.

During the processing time, and as described above, exosomes in the sample 114 may be lysed in the delay zone 116, which may free first targets 118, such as microRNAs. At least a portion of the sample 114, including first targets 118, may migrate to the conjugate pad 108 by lateral flow. The fluid sample 114 may dissolve an immobilization matrix to release first aptamers 120 conjugated to reporter molecules. First aptamers 120 may specifically bind first targets 118 to form first aptamer:first target complexes 122. The first aptamer:first target complexes 122 may migrate by lateral flow to the capture pad 110, where they may be bound by second aptamers 130 to form second aptamer:second target complexes 132.

Accumulation of second aptamer:second target complexes 132 may produce a visibly detectable signal or signals. For example, as depicted in FIG. 2E, the generation of two lines may indicate the presence of both at least one first target-control 118c and at least one first target-up 118a. The generation of a single line (not shown) may indicate the presence of only at least one first target-control 118c. As another example, and with reference to FIGS. 2E-2G, the generation of a red line or lines may indicate the presence of at least one first target-up 118a and the generation of a blue line or lines may indicate the presence of at least one first target-control 118c. A signal indicating the presence of at least one first target-up 118a may indicate that parturition will initiate in the pregnant woman from whom the sample 114 was obtained within a certain timeframe, as described above. A lack of a signal indicating the presence of at least one first target-up 118a may indicate that parturition will not initiate in the pregnant woman from whom the sample 114 was obtained within a certain timeframe, as described above. The absence of any signal may indicate that no or too few first targets 118 were present in the sample 114, or that the lateral flow device 100 did not operate as designed.

By way of example, but not limitation, the lateral flow device 100 of FIGS. 3A-3J may be used to determine the onset of parturition according to the procedure described above for the lateral flow device 100 of FIGS. 2A-2G in all aspects except for the following.

As depicted in FIGS. 3E-3J and as described in more detail above, the generation of a signal may indicate the presence of at least one first target-up 118a in the sample 114. The generation of a separate signal may indicate the presence of a least one first target-down 118b in the sample 114. A signal indicating the presence of at least one first target-up 118a may indicate that parturition will initiate in the pregnant woman from whom the sample 114 was obtained within a certain timeframe, as described above. A lack of a signal indicating the presence of at least one first target-up 118a, and/or the presence of a signal indicating the presence of at least one first target-down 118b, may indicate that parturition will not initiate in the pregnant woman from whom the sample 114 was obtained within a certain timeframe, as described above. The absence of any signal may indicate that no or too few first targets 118 were present in the sample 114, or that the lateral flow device 100 did not operate as designed.

The lateral flow devices 100 of FIGS. 2A-2G or 3A-3J may be used in conjunction with a vessel 140 for exosome lysis. By way of example, but not limitation, the vessel 140 of FIG. 4 may be used to lyse exosomes according to the following procedure. The lysis may be performed in a private setting, such as in a home, or in a medical environment, such as a doctor's office. The lysis may be conducted by a pregnant women using her own sample (described below), by non-medical personnel assisting a pregnant woman, or by medical personnel.

A sample 114 is added to the vessel 140. The sample 114 may be any bodily fluid such as urine, blood, saliva, plasma, amniotic fluid, and peritoneal fluid. The sample 114 may be applied dropwise, by pouring the sample 114 into the vessel 140, or by otherwise transferring the sample 114 to the vessel 140. When the sample 114 is urine, the sample 114 may be added to the vessel 140 by urinating into the vessel 140. The vessel 140 may include a visible mark, such as a line, that indicates how much sample 114 should be added to the vessel 140.

Detergent solution 142 may already be present in or may be added to the vessel 140. When detergent solution 142 is added to the vessel 140, it may be added by pouring in a predetermined amount. The sample 114 and detergent solution 142 may be mixed, such as by stirring, such as with a disposable stirrer. The sample 114 and detergent solution 142 may then be incubated at room temperature for a predetermined amount of time. The incubation period may be 1-10 minutes, 1-5 minutes, 1-3 minutes, less than 5 minutes, or less than 3 minutes. During the incubation period, and as described above, exosomes in the sample 114 may be lysed, which may free first targets 118, such as microRNAs.

The detergent solution 142 plus sample 114 comprising liberated first targets 118 may be applied to the sample pad 106 of a lateral flow device 100 of FIGS. 2A-2G or 3A-3J. The detergent solution 142 plus sample 114 may be applied by dipping the end of the device 100 comprising the sample pad 106 into the vessel 140 or by applying a small volume of sample 114 comprising liberated first targets 118 to the sample pad 106 with, for example, a disposable plastic bulb pipet. When used in conjunction with a vessel 140, the delay zone 116 of the sample pad 106 of FIGS. 2A-2G or 3A-3J may not include a detergent.

Following application of a sample 114, the user may not need to provide any input to the lateral flow device 100. The lateral flow device 100 may operate according to any of the procedures described above.

In the construction and operation of any of the devices and methods described above, the presently disclosed assay may predict the onset of labor, which may provide numerous benefits to pregnant women and/or their families. For example, the assay may remove uncertainty regarding timing, enable planning for labor and delivery in both personal and professional environments, allow a woman to avoid uncomfortable or awkward situations concomitant with the unexpected onset of labor, and satisfy curiosity. The assay may also benefit medical staff and associated professionals by enabling them to plan for the labor and delivery of pregnant women.

Components of Antibody-Based Lateral Flow Device

In another embodiment, the presently disclosed assay to predict the initiation of parturition may be performed using a lateral flow device 200 as depicted in FIGS. 5A-5E.

The backing 202, membrane 204, sample pad 206, absorbent pad 212, and delay zone 216 of the lateral flow device 200 are as described above for the lateral flow device 100 of FIGS. 2A-2G.

The conjugate pad 208 may include one or more first antibodies 220, each of which may be selective for a control target 218c or a first target-up 218a, which is a target that is up-regulated near the onset of parturition. Control targets 218c and first targets-up 218a may be any targets described above for control targets 118c and first targets-up 118a, respectively.

The first antibodies 220 may be immobilized on the conjugate pad 208, such as in a salt-sugar matrix, as described above for first aptamers 120. Also as described above for first aptamers 120, the first antibodies 220 may be conjugated to a molecule that will aid in detection, directly or indirectly, of the first antibody:first target complexes 222. The first antibodies 220 may be conjugated to gold nanoparticles, latex, or biotin. A subset of first antibodies 220, such as those that bind first targets-up 218a (hereinafter, "first antibody-up" 220a), may be conjugated to one reporter molecule and another subset of first antibodies 220, such as those that bind control targets 218c (hereinafter "first antibody-control" 220c), may be conjugated to a different reporter molecule. For example, first antibodies-up 220a may be conjugated to gold nanoparticles, and first antibodies-control 220c may be conjugated to latex.

The capture pad 210 may comprise a test zone 224 and a control zone 226. The capture pad 210 may include one or more second antibodies 230, each of which may be selective for a first antibody:first target complex 222. For example, a second antibody 230 may be selective for the first antibody: miR-200a complex. The second antibodies 230 may include a first subset that binds first antibody:first target-up complexes 222a (hereinafter, "second antibody-up" 230a). The second antibodies 230 may include another subset that binds first antibody:control target complexes 222c (hereinafter, "second antibody-control" 230c).

The second antibodies 230 may be immobilized on the capture pad 210, such as in a matrix. The matrix may facilitate binding of second antibodies 230 to first antibody: first target complexes 222. The matrix may also help prevent the second antibodies 230 from migrating, even in the presence of a fluid. The matrix may be glass fibers.

The second antibodies 230 may be immobilized within the capture pad 210 in any arrangement or grouping. Various arrangements and groupings, in conjunction with the conjugation of first antibodies 220 to detectable molecules, may help produce a variety of assay result presentations. The assay results may indicate the proximity of the onset of labor or the proper functioning of the device 200 as described in more detail below.

In one embodiment, all second antibodies-up 230a may be immobilized at a location within the capture pad 210 that is distinct from the location of immobilization of all second antibodies-control 230c. For example, and with reference to FIGS. 5A-5E, second antibodies 230 that bind first antibody: first target-up complexes 222a may be immobilized in a test zone 224. Second antibodies 230 that bind first antibody: control target complexes 222c may be immobilized in a control zone 226.

In another embodiment (not shown), each second antibody 230 that binds a first antibody:first target-up complex 222a may be immobilized separately. (See, e.g., FIGS. 2F and 2G for an example of how this embodiment may be configured.) Each second antibody 230 that binds a first antibody:control target complex 222c may also be immobilized separately.

In one implementation (not shown), each second antibody 230 may be immobilized in close proximity to the other second antibodies 230, such as in a single ladder-like pattern. (See, e.g., FIGS. 2F and 2G for an example of how this embodiment may be configured.) The second antibodies 230 may be immobilized in any location or combination of locations as described for second aptamers 130 above.

In another embodiment, the presently disclosed assay to predict the initiation of parturition may be performed using a lateral flow device 200 as depicted in FIGS. 6A-6G. The backing 202, membrane 204, sample pad 206, conjugate pad 208, capture pad 210, absorbent pad 212, and delay zone 216 of the lateral flow device 200 are as described above for FIGS. 5A-5E.

The conjugate pad 208 of the embodiment depicted in FIGS. 5A-5E may include one or more first antibodies 220, each of which may be selective for a first target-up 218a or a first target-down 218b. First targets-up 218a may include, but are not limited to, microRNAs such as miR-200a, miR-200b, and miR-429. First targets-down 218b may include, but are not limited to, miR-199a-3p, and miR-214.

The first antibodies 220 may be immobilized on the conjugate pad 208, such as in a salt-sugar matrix. The matrix may facilitate binding of microRNAs to the first antibodies 220.

The first antibodies 220 may be conjugated to a molecule that will aid in detection, directly or indirectly, of the first antibody:first target complexes 222. The molecules may include, but are not limited to, optical dyes, colored particles, fluorescent molecules, luminescent molecules, or phosphorescent molecules. For example, the first antibodies 220 may be conjugated to gold nanoparticles, latex, or biotin. A subset of first antibodies 220, such as first antibodies-up 220a, may be conjugated to one reporter molecule and another subset of first antibodies 220, such as those that bind first targets-down 218b (hereinafter "first antibody-down" 220b), may be conjugated to a different reporter molecule. For example, first antibodies-up 220a may be conjugated to gold nanoparticles, and first antibodies-down 220b may be conjugated to latex.

The capture pad 210 may comprise a test zone 224 and a control zone 226. The capture pad 210 may include one or more second antibodies 230, each of which may be selective for a first antibody:first target complex 222. For example, a second antibody 230 may be selective for the first antibody: miR-200a complex. The second antibodies 230 may include a first subset that binds first antibody:first target-up complexes 222a (hereinafter, "second antibody-up" 230a). The second antibodies 230 may include another subset that binds first antibody:first target-down complexes 222b (hereinafter, "second antibody-down" 230b).

The second antibodies 230 may be immobilized on the capture pad 210, such as in a matrix. The matrix may facilitate binding of second antibodies 230 to first antibody:first target complexes 222. The matrix may also help prevent the second antibodies 230 from migrating, even in the presence of a fluid. The matrix may be glass fibers.

The second antibodies 230 may be immobilized within the capture pad 210 in any arrangement or grouping. Various arrangements and groupings, in conjunction with the conjugation of first antibodies 220 to detectable molecules, may help produce a variety of assay result presentations. The assay results may indicate the proximity of the onset of labor or the proper functioning of the device 200 as described in more detail below.

In one embodiment, all second antibodies-up 230a may be immobilized at a location within the capture pad 210 that is distinct from the location of immobilization of all second antibodies-down 230b. For example, and with reference to FIGS. 3A-3G, second antibodies 230 that bind first antibody:first target-up complexes 222a may be immobilized in a test zone 224. Second antibodies 230 that bind first antibody:first target-down complexes 222b may be immobilized in a control zone 226.

In another embodiment (not shown), each second antibody 230 that binds a first antibody:first target-up complex 222a may be immobilized separately. (See, e.g., FIGS. 3H-3J for an example of how this embodiment may be configured.) Second antibodies 230 that bind first antibody:first target-down complexes 222b may also be immobilized separately.

In one implementation (not shown), each second antibody 230 may be immobilized in close proximity to the other second aptamers 230, such as in a single ladder-like pattern. (See, e.g., FIGS. 3H-3J for an example of how this embodiment may be configured.) The second antibodies 230 may be immobilized in any location or combination of locations as described for second aptamers 130 above.

In another embodiment, and as shown in FIG. 4, the presently disclosed assay to predict the initiation of parturition may include a vessel 140 for exosome lysis separate from the lateral flow device 200 of FIGS. 5A-5E or 6A-6G. The vessel 140, detergent solution 142, and sample 114 are as described above.

The sample pad 206 of the lateral flow devices 200 of FIGS. 5A-5E or 6A-6G may be configured to receive the detergent solution 142 with sample 114 comprising liberated first targets 118. In the present embodiment, the delay zones 216 of the sample pads 206 of FIGS. 5A-5E or 6A-6G may not include detergents.

Operation of the Antibody-Based Lateral Flow Device

By way of example, but not limitation, the lateral flow device 200 of FIGS. 5A-5E may operate according to the following procedure. A fluid sample 214 is applied to the sample 206 and retained in the delay zone 216 as described above for the aptamer-based lateral flow device 100 depicted in FIGS. 2A-2G.

In the conjugate pad 208, the fluid sample 214 dissolves the matrix, thereby releasing first antibodies 220 conjugated to reporter molecules. A subset of first antibodies 220, such as first antibodies-up 220a, is conjugated to one type of reporter molecule, such as gold nanoparticles. A second subset of first antibodies 220, such as first antibodies-control 220c, is conjugated to another type of reporter molecule, such as latex. The first antibodies 220 bind their first targets 218, if present, to form first antibody:first target complexes 222. The first antibody:first target complexes 222 may be first antibody:first target-up complexes 222a similar to first aptamer:first target-up complexes 122a described above. The first antibody:first target complexes 222 may be first antibody:first target-control complexes 222c similar to first aptamer:first target-control complexes 122c described above.

The first antibody:first target complexes 222 migrate via lateral flow through the conjugate pad 208 to the capture pad 210. In the capture pad 210, the second antibodies 230 bind their targets, if present, to form second antibody:second target complexes 232.

The second antibody:second target complexes 232 may be second antibody:second target-up complexes 232a similar to the second aptamer:second target-up complexes 132a described above. The second antibody:second target complexes 232 may be second antibody:second target-control complexes 232c similar to the second aptamer:second target-control complexes 132c described above.

The second antibody:second target complexes 232 may remain stationary on the capture pad 210 at the area of immobilization of the respective second antibodies 230. The accumulation of multiple second antibody:second target complexes 232 may result in a detectable signal. Detectable signals are as described above for the aptamer-based lateral flow device 100.

Figure 5A:
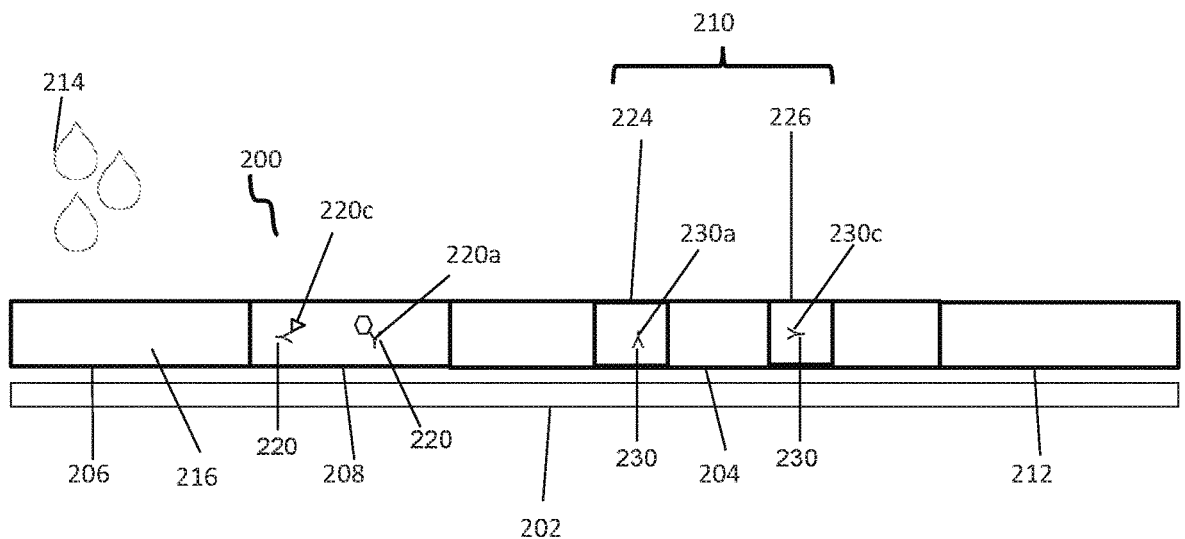
FIG. 5A is a schematic diagram of a lateral flow device according to another embodiment.
Figure 5B:
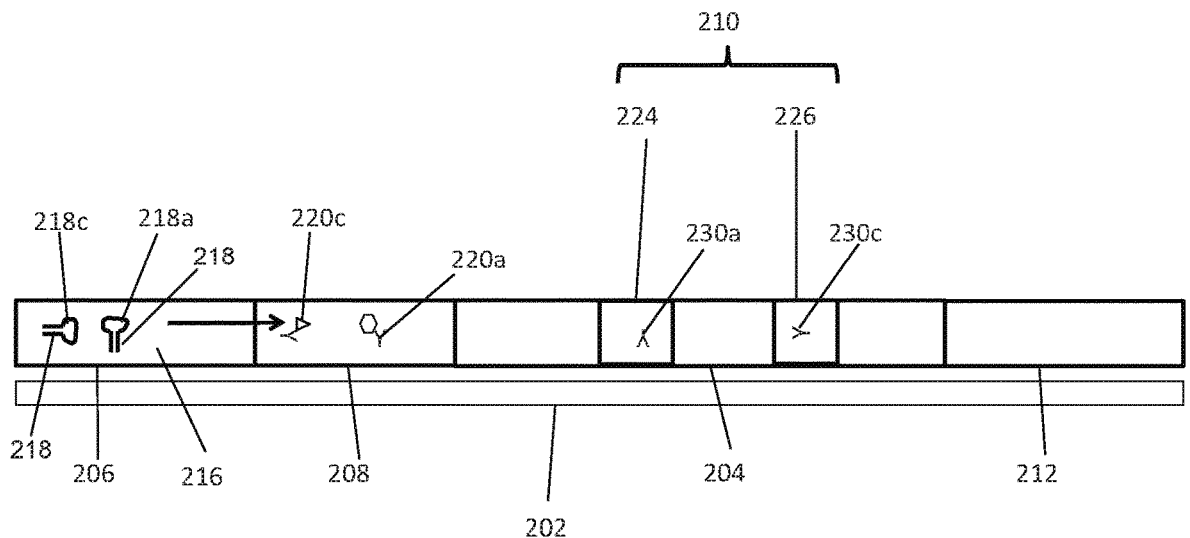
FIG. 5B is a schematic diagram of the lateral flow device of FIG. 5A after a sample has been applied.
Figure 5C:
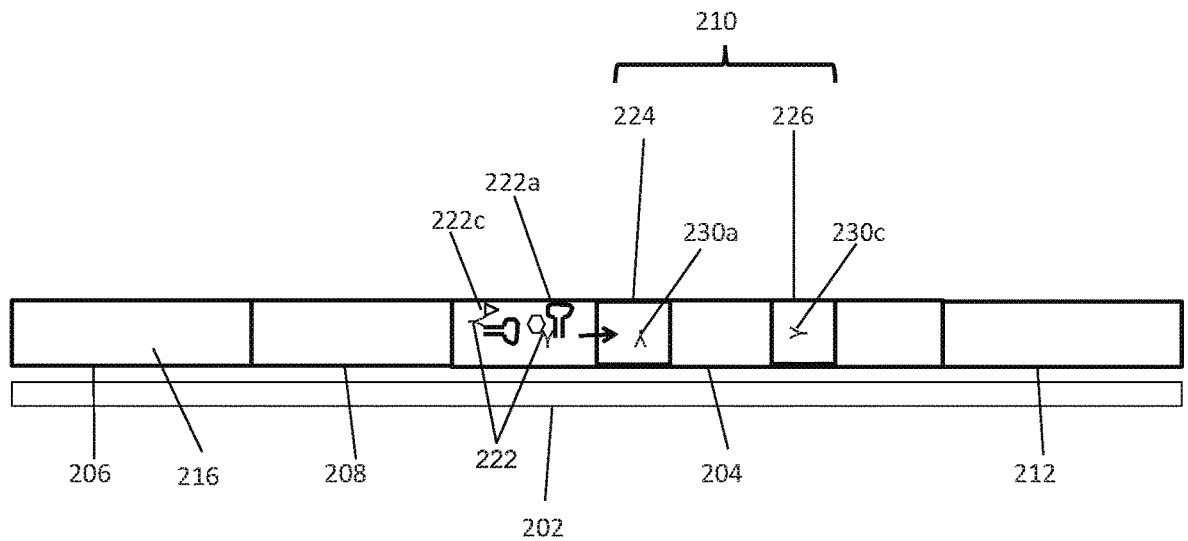
FIG. 5C is a schematic diagram of the lateral flow device of FIG. 5B after antibody:target complexes have migrated along the assay.
Figure 5D:
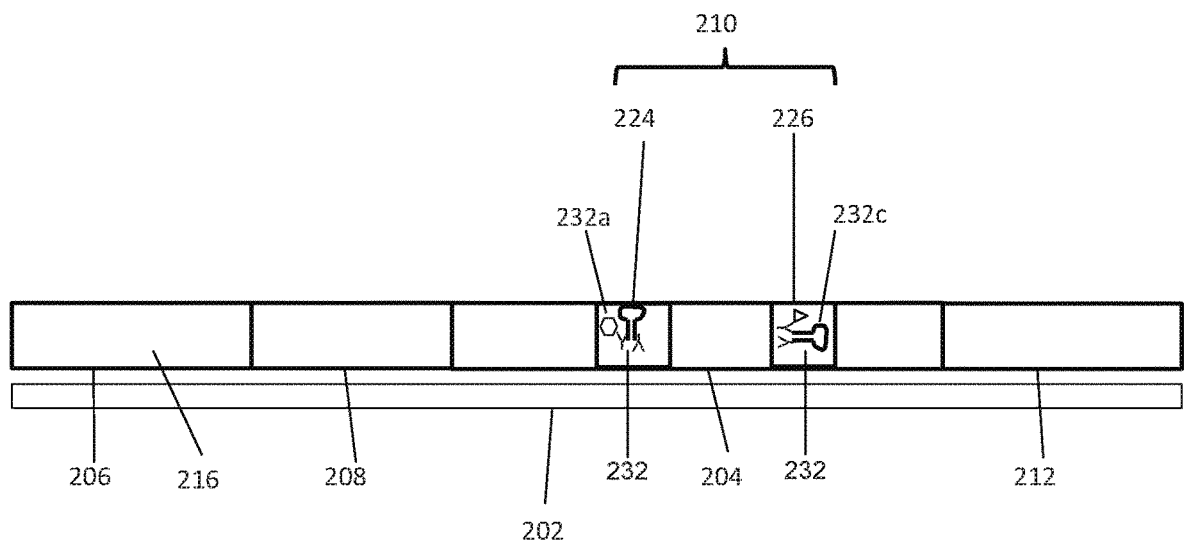
FIG. 5D is a schematic diagram of the lateral flow device of FIG. 5C after a second antibody:second target complex has formed.
Figure 5E:
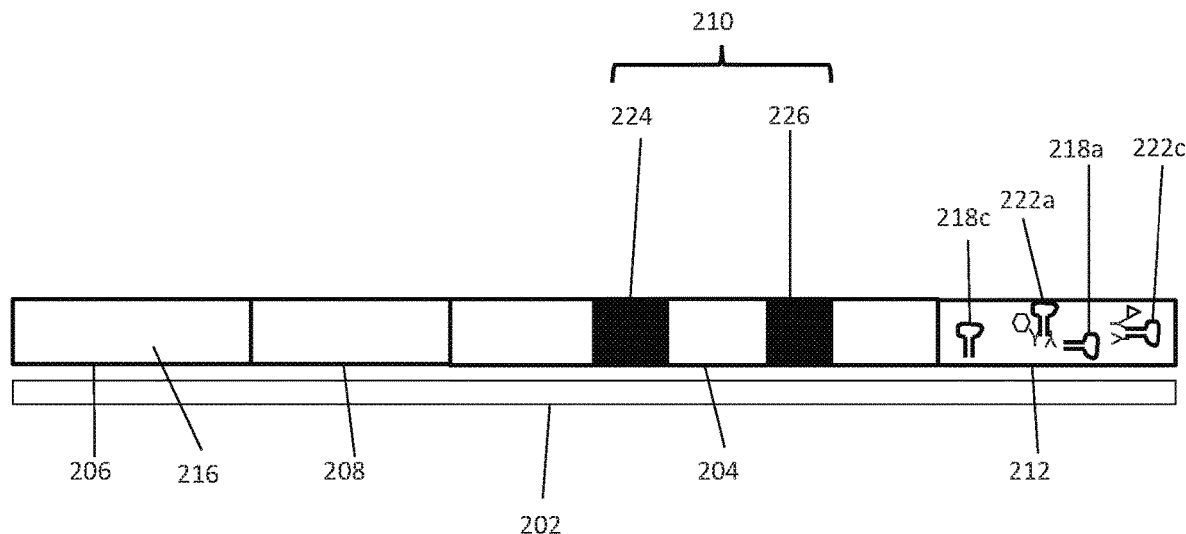
FIG. 5E is a schematic diagram of the lateral flow device of FIG. 5A showing test results according to one embodiment.

In the embodiment depicted in FIG. 5E, one signal is produced for all second antibody:second target-up complexes 232a, if present. A separate signal is produced for all second antibody:second target-control complexes 232c, if present. The signals may be distinct from each other or the same as each other as described above for FIG. 2E.

The signals may convey assay results. For example, as depicted in FIG. 5E, a signal at the test zone 224 may indicate that at least one first target-up 218a is present in the sample 214. A signal at the control zone 226 may indicate that at least one first target-control 218c is present in the sample 214.

In one embodiment, and as shown in FIG. 5E, binary results may be produced. The presence of a signal in the test zone 224 may indicate that the initiation of parturition is near. The absence of a signal (not shown) in the test zone 224 may indicate that the initiation of parturition is not near. Without being limited to any mechanism of mode of action, the result depicted in FIG. 5E may indicate that parturition is near because the parturition signaling cascade has led to an increase in first targets-up 218a to levels detectable in the sample 214. The absence of a signal (not shown) in the test zone 224 may indicate that the initiation of parturition is not near because the first targets-up 218a are not yet at detectable levels in the sample 214. Binary assay results may indicate a specific timeframe for the onset of parturition as described above for the aptamer-based lateral flow device 100.

In another embodiment, signals or results produced by the lateral flow device 200 of FIG. 5A may be as described above for the lateral flow device 100 of FIGS. 2F and 2G. Briefly, a separate signal may be produced for each second antibody:second target-up complex 232a that is present and for each second antibody:second target-control complex 232c that is present.

The design of the antibody-based lateral flow device 200 may affect the meaning of the assay results similarly to how the design of the aptamer-based lateral flow device 100 may affect the meaning of the assay results as described above.

As for the aptamer-based lateral flow devices 100 and as described above, the absence of any signal in the instant embodiment of an antibody-based lateral flow device 200 may indicate that no or too few first targets 218 were present in the sample 214, or that the lateral flow device 200 did not operate as designed.

By way of example, but not limitation, the antibody-based lateral flow device 200 of FIGS. 6A-6G may operate according to the following procedure. First targets 218 migrate toward a conjugate pad 208 after being liberated from a sample 214 that has been applied to a sample pad 206 according to the procedure described above for the aptamer-based lateral flow device 100 depicted in FIGS. 2A-2G.

In the conjugate pad 208, the fluid sample 214 dissolves the matrix, thereby releasing first antibodies 220 conjugated to reporter molecules. A subset of first antibodies 220, such as first antibodies-up 220a, is conjugated to one type of reporter molecule, such as gold nanoparticles. A second subset of first antibodies 220, such as first antibodies-down 220b, is conjugated to another type of reporter molecule, such as latex. The first antibodies 220 bind their first targets 218, if present, to form first antibody:first target complexes 222. The first antibody:first target complexes 222 may be first antibody:first target-up complexes 222a similar to first aptamer:first target-up complexes 122a described above. The first antibody:first target complexes 222 may be first antibody:first target-down complexes 222b similar to first aptamer:first target-down complexes 122b described above.

The first antibody:first target complexes 222 migrate via lateral flow through the conjugate pad 208 to the capture pad 210. In the capture pad 210, the second antibodies 230 bind their targets, if present, to form second antibody:second target complexes 232.

The second antibody:second target complexes 232 may be second antibody:second target-up complexes 232a similar to the second aptamer:second target-up complexes 132a described above. The second antibody:second target complexes 232 may be second antibody:second target-down complexes 232b similar to the second aptamer:second target-down complexes 132b described above.

The second antibody:second target complexes 232 may remain stationary on the capture pad 210 at the area of immobilization of the respective second antibodies 230. The accumulation of multiple second antibody:second target complexes 232 may result in a detectable signal. Detectable signals are as described above for the aptamer-based lateral flow device 100.

Figure 6A:
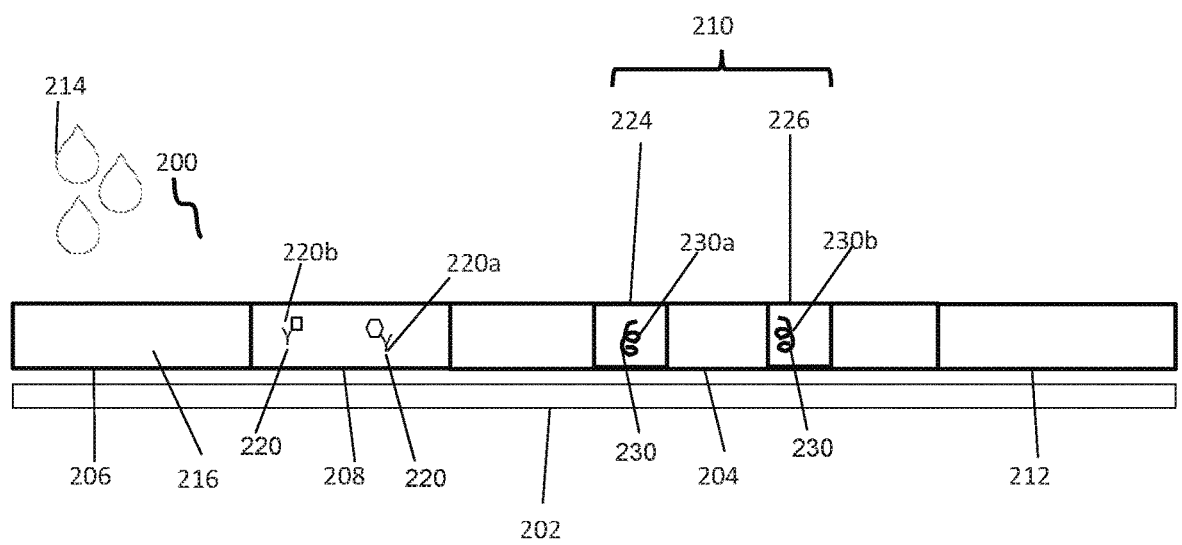
FIG. 6A is a schematic diagram of a lateral flow device according to another embodiment.
Figure 6B:
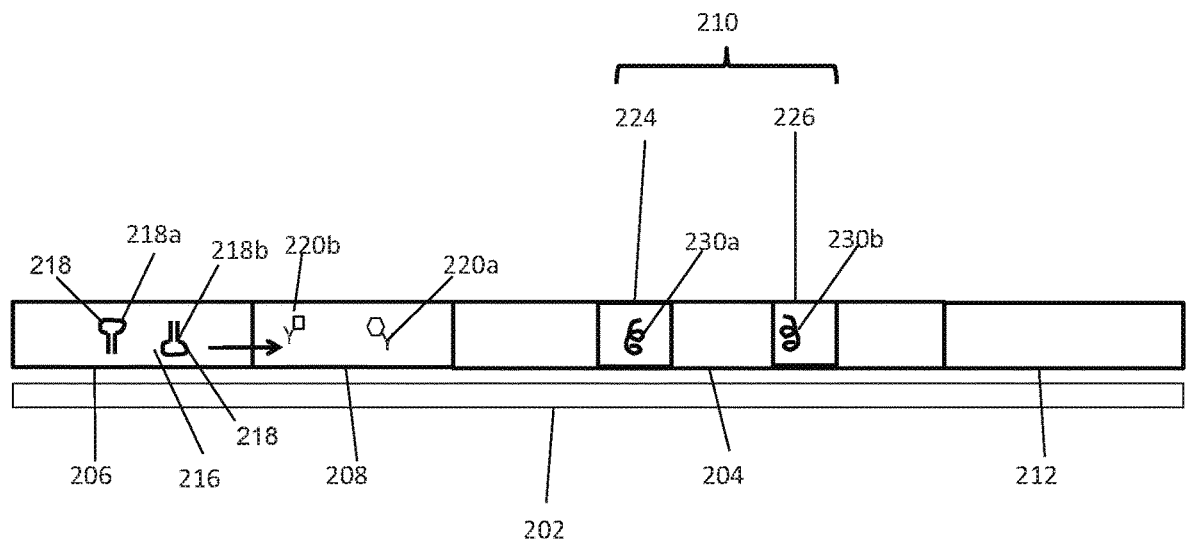
FIG. 6B is a schematic diagram of the lateral flow device of FIG. 6A after a sample has been applied.
Figure 6C:
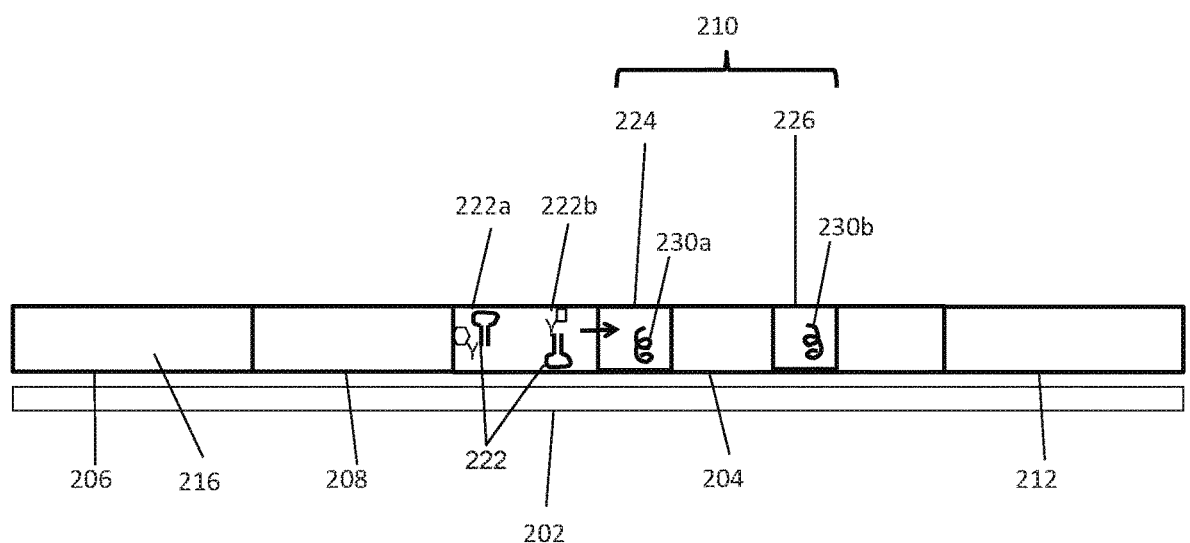
FIG. 6C is a schematic diagram of the lateral flow device of FIG. 6B after aptamer:target complexes have migrated along the device.
Figure 6D:
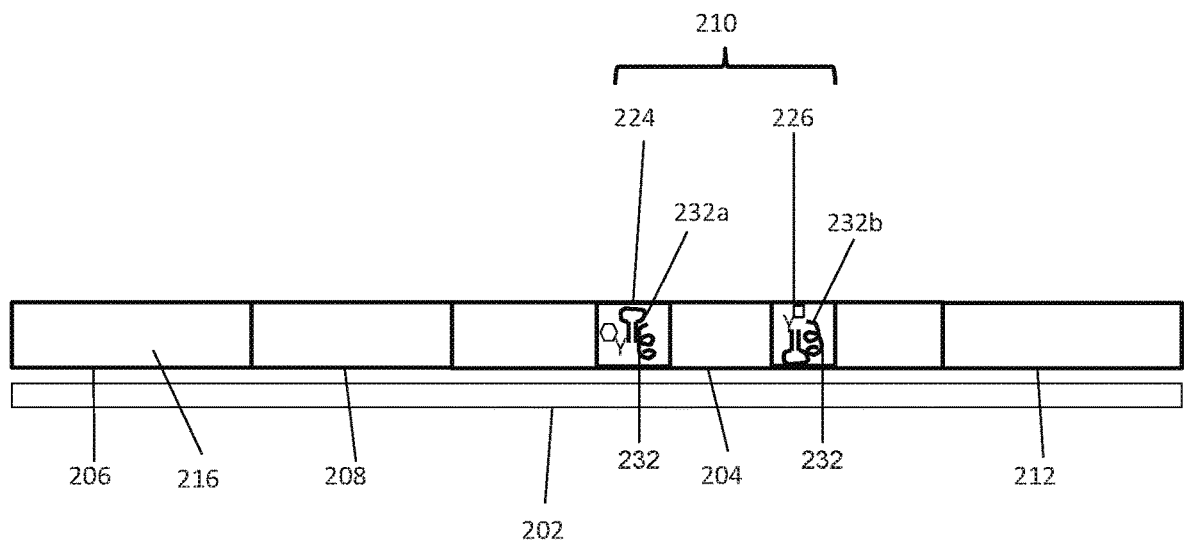
FIG. 6D is a schematic diagram of the lateral flow device of FIG. 6C after second antibody:second target complexes have formed.
Figure 6E:
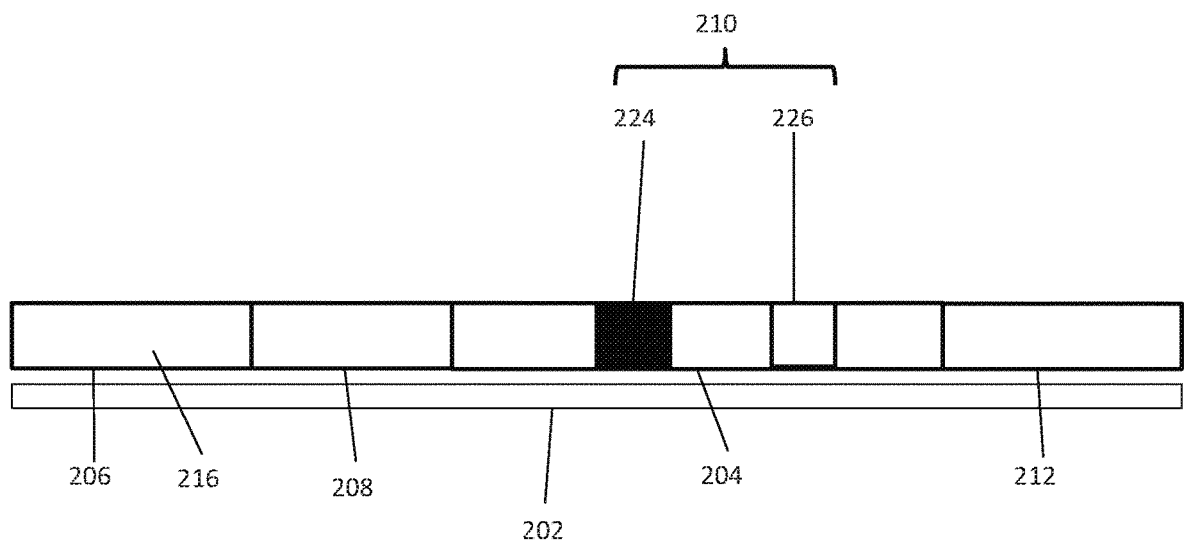
FIG. 6E is a schematic diagram of the lateral flow device of FIG. 6A showing test results according to one embodiment.
Figure 6F:
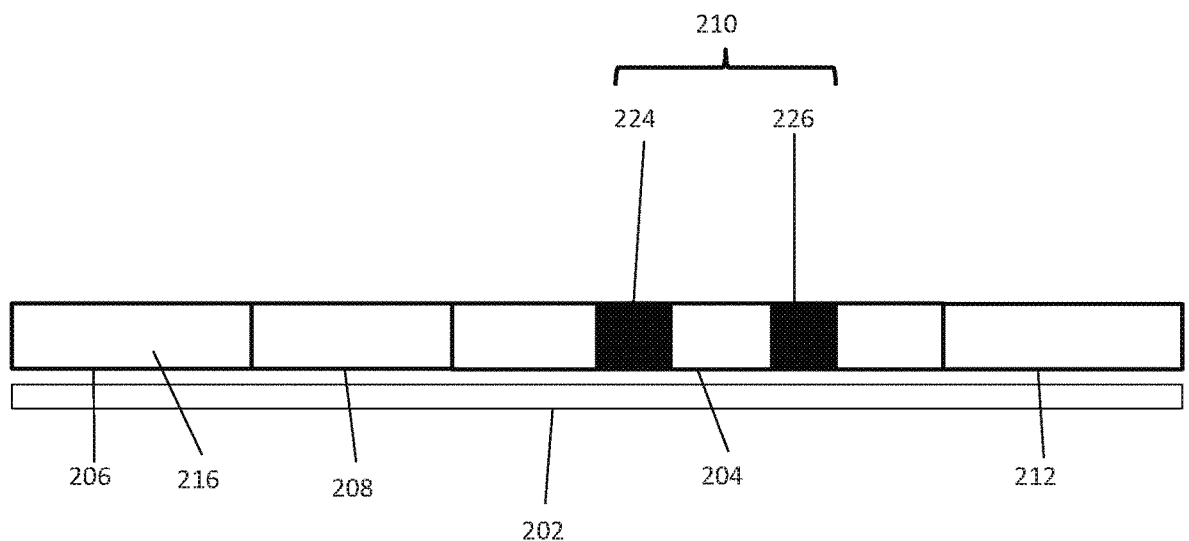
FIG. 6F is a schematic diagram of the lateral flow device of FIG. 6A showing test results according to another embodiment.
Figure 6G:
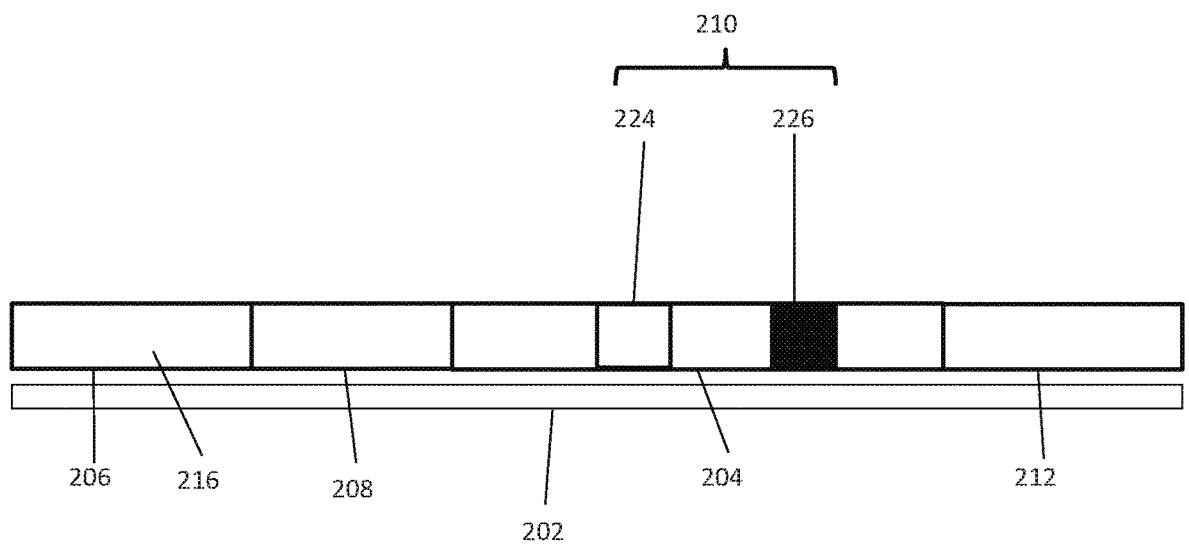
FIG. 6G is a schematic diagram of the lateral flow device of FIG. 6A showing test results according to another embodiment.

In the embodiments depicted in FIGS. 6E-6G, one signal is produced for all second antibody:second target-up complexes 232a, if present. A separate signal is produced for all second antibody:second target-down complexes 232b, if present. The signals may be similar to those described above for the aptamer-based lateral flow device 100 of FIGS. 3E-3G, and may convey assay results similarly to those described above for the aptamer-based lateral flow device 100 of FIGS. 3E-3G.

In another embodiment (not shown), a separate signal is produced for each second antibody:second target-up complex 232a that is present and for each second antibody:second target-down complex 232b that is present, similar to the signals described above for the lateral flow device 100 of FIGS. 3H-3J. The signals may be similar to those described above for the aptamer-based lateral flow device 100 of FIGS. 3H-3J, and may convey assay results similarly to those described above for the aptamer-based lateral flow device 100 of FIGS. 3H-3J.

The design of the antibody-based lateral flow device 200 may affect the meaning of the assay results similarly to how the design of the aptamer-based lateral flow device 100 may affect the meaning of the assay results as described above.

As for the aptamer-based lateral flow devices 100 and as described above, the absence of any signal in the instant embodiment of an antibody-based lateral flow device 200 may indicate that no or too few first targets 218 were present in the sample 214, or that the lateral flow device 200 did not operate as designed.

Methods of Use of the Antibody-Based Lateral Flow Device

By way of example, but not limitation, the lateral flow device 200 of FIGS. 5A-5E may be used to determine the onset of parturition according to the following procedure. In all aspects except those described below, the lateral flow device may be used as described above for the lateral flow device 100 of FIGS. 2A-2E.

Following application of a sample 214, exosomes in the sample 214 may be lysed in the delay zone 216, which may free first targets 218, such as microRNAs. At least a portion of the sample 214, including first targets 218, may migrate to the conjugate pad 208 by lateral flow. The fluid sample 214 may dissolve an immobilization matrix to release first antibodies 220 conjugated to reporter molecules. First antibodies 220 may specifically bind first targets 218 to form first antibody:first target complexes 222. The first antibody:first target complexes 222 may migrate by lateral flow to the capture pad 210, where they may be bound by second antibodies 230 to form second antibody:second target complexes 232.

Accumulation of second antibody:second target complexes 232 may produce a visibly detectable signal or signals as described above for the lateral flow device 100 of FIGS. 2E-2G.

By way of example, but not limitation, the lateral flow device 200 of FIGS. 6A-6G may be used to determine the onset of parturition according to the procedures described above for the lateral flow device 200 of FIGS. 5A-5E in all aspects except for the following.

As depicted in FIGS. 6E-6G and as described in more detail above, the generation of a signal may indicate the presence of at least one first target-up 218a in the sample 214. The generation of a separate signal may indicate the presence of a least one first target-down 218b in the sample 214. A signal indicating the presence of at least one first target-up 218a may indicate that parturition will initiate in the pregnant woman from whom the sample 214 was obtained within a certain timeframe, as described above. A lack of a signal indicating the presence of at least one first target-up 218a, and/or the presence of a signal indicating the presence of at least one first target-down 218b, may indicate that parturition will not initiate in the pregnant woman from whom the sample 214 was obtained within a certain timeframe, as described above. The absence of any signal may indicate that no or too few first targets 218 were present in the sample 214, or that the lateral flow device 200 did not operate as designed.

The lateral flow devices 200 of FIGS. 5A-5E or 6A-6G may be used in conjunction with a vessel 140 for exosome lysis. The vessel 140 of FIG. 4 may be used to lyse exosomes according to the procedure described above.

The detergent solution 142 plus sample 214 comprising liberated first targets 218 may be applied to the sample pad 206 of a lateral flow device 200 of FIGS. 5A-5E or 3A-3G. The detergent solution 142 plus sample 214 may be applied by dipping the end of the device 200 comprising the sample pad 206 into the vessel 140 or by applying a small volume of sample 214 comprising liberated first targets 218 to the sample pad 206 with, for example, a disposable plastic bulb pipet. When used in conjunction with a vessel 140, the delay zone 216 of the sample pad 206 of FIGS. 5A-5E or 3A-3G may not include a detergent.

Following application of a sample 214, the user may not need to provide any input to the lateral flow device 200. The lateral flow device 200 may operate according to any of the procedures described above.

In the construction and operation of any of the devices and methods described above, the presently disclosed assay may predict the onset of labor, which may provide numerous benefits to pregnant women and/or their families. For example, the assay may remove uncertainty regarding timing, enable planning for labor and delivery in both personal and professional environments, allow a woman to avoid uncomfortable or awkward situations concomitant with the unexpected onset of labor, and satisfy curiosity. The assay may also benefit medical staff and associated professionals by enabling them to plan for the labor and delivery of pregnant women.

Kits

In some embodiments, the presently disclosed assay for determining the onset of labor may be provided as a kit. A kit may include any of the aptamer-based lateral flow devices 100 or the antibody-based lateral flow devices 200 described above. In some embodiments, a kit also includes a vessel 140 and/or detergent solution 142 as shown in FIG. 4, and may also include a stirrer as described above. A kit may also include instructions for use.

In some embodiments, a kit is available as a direct-to-consumer device for determining the onset of labor. In the construction and use of a direct-to-consumer device, the ability to use the presently disclosed lateral flow devices 100, 200 at home, even when analyzing microRNAs, provides benefits such as convenience, ready accessibility, flexibility in timing and repetition of use, and privacy. In other embodiments, the kit is provided by or utilized by a medical professional, such as a physician or nurse.

EXAMPLES

Example 1—Aptamer Development

Aptamers are developed in a two-step process. First, aptamers are developed against microRNAs involved in the onset of parturition (miR-200a, miR-200b, miR-429, miR-199a-3p, and miR-214) and control microRNAs (miR-22-3p, miR-99a-5p, miR-99b-5p, miR-124-3p, and miR-128). Aptamers are developed by SELEX or other similar methods as described in Oliphant et al. (*Mol. Cell Biol.* 1989, 9:2944-2949), Tuerk & Gold (*Science* 1990, 249:505-510), Ellington & Szostak (*Nature* 1990, 346:818-822), and Lee et al. (*Mol. Ther.* 2013, 21:1004-1013).

The first set of aptamers bind microRNAs to form aptamer:microRNA complexes. Aptamer:microRNA complexes include aptamer:miR-200a, aptamer:miR-200b, aptamer:miR-429, aptamer:miR-199a-3p, aptamer:miR-214, aptamer:miR-22-3p, aptamer:miR-99a-5p, aptamer:miR-99b-5p, aptamer:miR-124-3p, and aptamer:miR-128. Each aptamer:microRNA complex then serves as the target for a second round of aptamer development. Each second aptamer is specific for an aptamer:microRNA complex.

Example 2—Aptamer-Based Lateral Flow Device with Control MicroRNAs

A lateral flow device 100 is constructed with a membrane 104, sample pad 106, conjugate pad 108, capture pad 110, and absorbent pad 112 mounted on a backing 102 as shown in FIGS. 2A-2E. The sample pad 106 is constructed with a delay zone of sucrose and detergents. First aptamers 120 specific to each of miR-200a, miR-200b, miR-429, miR-99b-5p, miR-128, and miR-124-3p are embedded in a salt-sugar matrix in the conjugate pad 108. The first aptamers 120 specific to miR-200a, miR-200b, and miR-429 are conjugated to gold nanoparticles. The first aptamers 120 specific to miR-99b-5p, miR-128, and miR-124-3p are conjugated to latex.

Second aptamers 130 specific to aptamer:miR-200a, aptamer:miR-200b, and aptamer:miR-429 complexes are immobilized together in a test zone 124, and second aptamers 130 specific to aptamer:miR-99b-5p, aptamer:miR-128, and aptamer:miR-124-3p complexes are immobilized together in a control zone 126.

A pregnant woman urinates on the sample pad 106 of the lateral flow device 100 and waits approximately 5 minutes for results to be available. A single line in each of the test zone 124 and the control zone 126 indicates that parturition will commence in the pregnant woman within 48 hours. A single line in the control zone 126 but no line in the test zone 124 indicates that parturition will not commence within 48 hours.

Example 3—Aptamer-Based Lateral Flow Device with Down-Regulated MicroRNAs

A lateral flow device 100 is constructed with a membrane 104, sample pad 106, conjugate pad 108, capture pad 110, and absorbent pad 112 mounted on a backing 102 as shown in FIGS. 3A-3G. The sample pad 106 is constructed with a delay zone of sucrose and detergents. First aptamers 120 specific to each of miR-200a, miR-200b, miR-429, miR-199a-3p, and miR-214 are embedded in a salt-sugar matrix in the conjugate pad 108. The first aptamers 120 specific to miR-200a, miR-200b, and miR-429 are conjugated to gold nanoparticles. The first aptamers 120 specific to miR-199a-3p and miR-214 are conjugated to latex.

Second aptamers 130 specific to aptamer:miR-200a, aptamer:miR-200b, and aptamer:miR-429 complexes are immobilized together in a test zone 124, and second aptamers 130 specific to aptamer: miR-199a-3p and aptamer: miR-214 complexes are immobilized together in a control zone 126.

A pregnant woman urinates on the sample pad 106 of the lateral flow device 100 and waits approximately 5 minutes for results to be available. A single line in the test zone 124 and the absence of a line in the control zone 126 indicates that parturition will commence in the pregnant woman within 36 hours. A single line in the control zone 126 but no line in the test zone 124 indicates that parturition will not commence within 36 hours. A single line in each of the test zone 124 and control zone 126 indicates that parturition will commence within 72 hours.

Example 4—Aptamer-Based Lateral Flow Device with Separate Exosome Lysis

A vessel 140 and detergent solution 142, as shown in FIG. 4, and a stirrer are provided with a lateral flow device 100 of FIGS. 2A-2G or 3A-3J as part of a kit. The vessel is a plastic cup, the detergent solution includes Triton™ X, and the stirrer is a disposable plastic stirrer.

A pregnant woman partially fills a vessel 140 by urinating into the vessel 140 until the urine sample 114 reaches a pre-marked line. A volume of detergent solution 142 is then added to the vessel 140, the fluid is stirred, and the vessel 140 is left to incubate at room temperature for approximately 3 minutes.

The end of a lateral flow device 100 comprising a sample pad 106 is dipped briefly into the vessel 140 to saturate the sample pad 106. Results are available in approximately 5 minutes, and may be displayed according to any of the descriptions provided above.

Example 5—Antibody Development

Antibodies are developed by the methods described in Harlow & Lane (*Antibodies: A Laboratory Manual* 1988, Cold Spring Harbor Laboratory, Cold Spring Harbor, N.Y.) or similar methods. Briefly, antibodies are developed in a two-step process. First, antibodies are developed against microRNAs involved in the onset of parturition (miR-200a, miR-200b, miR-429, miR-199a-3p, and miR-214) and against control microRNAs (miR-22-3p, miR-99a-5p, miR-99b-5p, miR-124-3p, and miR-128) by immunizing an animal with an immunogen comprising one of the foregoing microRNAs. Polyclonal antibodies are recovered from the serum of the immunized animals.

The first set of antibodies bind microRNAs to form antibody:microRNA complexes. Antibody:microRNA complexes include antibody:miR-200a, antibody:miR-200b, antibody:miR-429, antibody:miR-199a-3p, antibody:miR-214, antibody:miR-22-3p, antibody:miR-99a-5p, antibody:miR-99b-5p, antibody:miR-124-3p, and antibody:miR-128. Each antibody:microRNA complex then serves as the target for a second round of antibody development. Each second antibody is specific for an antibody:microRNA complex.

Example 6—Antibody-Based Lateral Flow Device with Control MicroRNAs

A lateral flow device 200 is constructed with a membrane 204, sample pad 206, conjugate pad 208, capture pad 210, and absorbent pad 212 mounted on a backing 202 as shown in FIGS. 5A-5E. The sample pad 206 is constructed with a delay zone of sucrose and detergents. First antibodies 220 specific to each of miR-200a, miR-200b, miR-429, miR-99b-5p, miR-128, and miR-124-3p are embedded in a salt-sugar matrix in the conjugate pad 208. The first antibodies 220 specific to miR-200a, miR-200b, and miR-429 are conjugated to gold nanoparticles. The first antibodies 220 specific to miR-99b-5p, miR-128, and miR-124-3p are conjugated to latex.

Second antibodies 230 specific to antibody:miR-200a, antibody:miR-200b, and antibody:miR-429 complexes are immobilized together in a test zone 224, and second antibodies 230 specific to antibody:miR-99b-5p, antibody:miR-128, and antibody:miR-124-3p complexes are immobilized together in a control zone 226.

A pregnant woman urinates on the sample pad 206 of the lateral flow device 200 and waits approximately 5 minutes for results to be available. A single line in each of the test zone 224 and the control zone 226 indicates that parturition will commence in the pregnant woman within 48 hours. A single line in the control zone 226 but no line in the test zone 224 indicates that parturition will not commence within 48 hours.

Example 7—Antibody-Based Lateral Flow Device with Down-Regulated MicroRNAs

A lateral flow device 200 is constructed with a membrane 204, sample pad 206, conjugate pad 208, capture pad 210, and absorbent pad 212 mounted on a backing 202 as shown in FIGS. 6A-6G. The sample pad 206 is constructed with a delay zone of sucrose and detergents. First antibodies 220 specific to each of miR-200a, miR-200b, miR-429, miR-199a-3p, and miR-214 are embedded in a salt-sugar matrix in the conjugate pad 208. The first antibodies 220 specific to miR-200a, miR-200b, and miR-429 are conjugated to gold nanoparticles. The first antibodies 220 specific to miR-199a-3p and miR-214 are conjugated to latex.

Second antibodies 230 specific to antibody:miR-200a, antibody:miR-200b, and antibody:miR-429 complexes are immobilized together in a test zone 224, and second antibodies 230 specific to antibody:miR-199a-3p and antibody:miR-214 complexes are immobilized together in a control zone 226.

A pregnant woman urinates on the sample pad 206 of the lateral flow device 200 and waits approximately 5 minutes for results to be available. A single line in the test zone 224 and the absence of a line in the control zone 226 indicates that parturition will commence in the pregnant woman within 36 hours. A single line in the control zone 226 but no line in the test zone 224 indicates that parturition will not commence within 36 hours.

A single line in each of the test zone 224 and control zone 226 indicates that parturition will commence within 72 hours.

Example 8—Antibody-Based Lateral Flow Device with Separate Exosome Lysis

A vessel 140 and detergent solution 142, as shown in FIG. 4, and a stirrer (not shown) are provided with a lateral flow device 200 of FIGS. 2A-2G or 3A-3J as part of a kit. The vessel is a plastic cup, the detergent solution includes Triton™ X, and the stirrer is a disposable plastic stirrer.

A pregnant woman partially fills a vessel 140 by urinating into the vessel 140 until the urine sample 214 reaches a pre-marked line. A volume of detergent solution 142 is then added to the vessel 140, the fluid is stirred, and the vessel 140 is left to incubate at room temperature for approximately 3 minutes.

The end of a lateral flow device 200 comprising a sample pad 206 is dipped briefly into the vessel 140 to saturate the sample pad 206. Results are available in approximately 5 minutes, and may be displayed according to any of the descriptions provided above.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of the disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the disclosure as defined in the claims. Although various embodiments have been described above with a certain degree of particularity, or with reference to one or more individual embodiments, those skilled in the art could make numerous alterations to the disclosed embodiments without departing from the spirit or scope of the present disclosure. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the disclosure as defined in the following claims.

What is claimed is:

1. A lateral flow device for predicting the initiation of parturition comprising:
    a sample pad;
    a conjugate pad to which a plurality of first associators are releasably bound, the plurality of first associators capable of binding a microRNA; and
    a capture pad to which a plurality of second associators are fixedly bound,
    wherein at least one of the first associator and second associator is an aptamer and the other of the first associator and second associator is selected from an aptamer and an antibody.

2. The device of claim 1, wherein the expression level of the microRNA is increased in the initiation of parturition.

3. The device of claim 1, wherein the microRNA is selected from miR-429, miR-200a, and miR-200b.

4. The device of claim 1, wherein the expression level of the microRNA is decreased in the initiation of parturition.

5. The device of claim 1, wherein the microRNA is selected from miR-199a-3p and miR-214.

6. The device of claim 1, wherein each associator in the plurality of first associators is conjugated to a reporter molecule.

7. The device of claim 6, wherein the reporter molecule is selected from a gold nanoparticle and latex.

8. The device of claim 1, wherein each associator in the plurality of second associators is capable of binding a complex of the first associator bound to the microRNA.

9. The device of claim 1, wherein the sample pad may receive a sample from a pregnant woman and the sample is selected from urine, blood, saliva, plasma, amniotic fluid, and peritoneal fluid.

10. The device of claim 9, wherein the sample comprises exosomes.

11. The device of claim 10, wherein the sample pad comprises a delay zone comprising an exosome-lysing detergent.

12. A method of predicting the initiation of parturition comprising:
    providing the lateral flow device of claim 1, and
    applying a sample to the device, the sample comprising the microRNA,
    wherein the microRNA contact the plurality of first associators to form first complexes,
    wherein the first complexes contact the plurality of second associators to form second complexes, and
    wherein the formation of second complexes produces a signal that provides a prediction of the initiation of parturition .

13. The method of claim 12, wherein the first associators are conjugated to reporter molecules and the detectable signal is a visually detectable signal.

14. The method of claim 12, comprising incubating the sample in an exosome-lysing detergent prior to contacting with the plurality of first associators.

15. A kit for predicting the initiation of parturition comprising:
    a lateral flow device comprising:
        a sample pad;
        a conjugate pad to which a plurality of first associators are releasably bound, the plurality of first associators capable of binding a microRNA; and
        a capture pad to which a plurality of second associators are fixedly bound,
        wherein at least one of the first associator and second associator is an aptamer and the other of the first associator and second associator is selected from an aptamer and an antibody;
    a sample vessel;
    a detergent solution; and
    instructions for using the device.

16. The kit of claim 15, wherein the lateral flow device comprises a backing affixed to each of the sample pad, the conjugate pad, and the capture pad .

* * * * *